(12) United States Patent
Morita et al.

(10) Patent No.: US 12,345,663 B2
(45) Date of Patent: Jul. 1, 2025

(54) REINFORCEMENT BAR CORROSION EVALUATION DEVICE, REINFORCEMENT BAR CORROSION EVALUATION METHOD, AND COMPUTER PROGRAM

(71) Applicant: GEO SEARCH CO., LTD., Tokyo (JP)

(72) Inventors: Hideaki Morita, Tokyo (JP); Yoko Taki, Tokyo (JP); Yukio Ozawa, Tokyo (JP); Masahiko Ota, Tokyo (JP)

(73) Assignee: GEO SEARCH CO., LTD., Tokyo (JP)

( * ) Notice: Subject to any disclaimer, the term of this patent is extended or adjusted under 35 U.S.C. 154(b) by 335 days.

(21) Appl. No.: 17/778,092

(22) PCT Filed: Jun. 18, 2020

(86) PCT No.: PCT/JP2020/023929
§ 371 (c)(1),
(2) Date: May 19, 2022

(87) PCT Pub. No.: WO2021/100230
PCT Pub. Date: May 27, 2021

(65) Prior Publication Data
US 2022/0412875 A1    Dec. 29, 2022

(30) Foreign Application Priority Data
Nov. 21, 2019 (JP) .................. 2019-210215

(51) Int. Cl.
*G01N 22/02*   (2006.01)
*G01N 17/00*   (2006.01)
(Continued)

(52) U.S. Cl.
CPC ........... *G01N 22/02* (2013.01); *G01N 17/006* (2013.01); *G01N 22/00* (2013.01); *G01N 33/383* (2013.01)

(58) Field of Classification Search
CPC .... G01N 33/383; G01N 17/006; G01N 22/02; G01N 22/00
(Continued)

(56) References Cited

U.S. PATENT DOCUMENTS

2018/0017531 A1* 1/2018 Juhnke .................. G01N 29/12

FOREIGN PATENT DOCUMENTS

| JP | S6117051 A | 1/1986 |
| JP | 2000-028583 A | 1/2000 |

(Continued)

OTHER PUBLICATIONS

Search Report and Written Opinion in International Application No. PCT/JP2020/023929 dated Aug. 4, 2020, 7 pages.

*Primary Examiner* — John Fitzgerald
*Assistant Examiner* — Truong D Phan
(74) *Attorney, Agent, or Firm* — MARSHALL, GERSTEIN & BORUN LLP

(57) ABSTRACT

A reinforcement bar corrosion evaluation device capable of efficiently and quantitatively evaluating a degree of corrosion of reinforcement bar in a reinforced concrete (RC) deck bridge includes: an acquisition section configured to acquire reflection response data related to a reflection response of electromagnetic waves irradiated from a surface of the reinforced concrete deck bridge in a depth direction of a deck panel, a removal section configured to remove a surface frequency component obtained by the electromagnetic waves being reflected at an asphalt concrete layer of the deck panel from a frequency distribution of a reflection response expressing the reflection response data acquired by the acquisition section, and an evaluation section configured to evaluate a degree of corrosion of the reinforcement bar in the deck panel by using a first measurement peak value in the frequency distribution of the reflection response from (Continued)

which the surface frequency component has been removed by the removal section, which is a peak value of a level of a frequency component of a first frequency band, and using a second measurement peak value therein, which is a peak value of a level of a frequency component of a second frequency band that is a higher frequency band than the first frequency band.

9 Claims, 28 Drawing Sheets

(51) Int. Cl.
 *G01N 22/00* (2006.01)
 *G01N 33/38* (2006.01)
(58) Field of Classification Search
 USPC .................. 73/643, 610, 614, 616, 865.8
 See application file for complete search history.

(56) References Cited

FOREIGN PATENT DOCUMENTS

| | | | | |
|---|---|---|---|---|
| JP | 2005043197 A | * | 2/2005 | |
| JP | 4603599 B2 | * | 12/2010 | ............. G01B 17/02 |
| JP | 2016-188545 A | | 11/2016 | |
| JP | 2016-191697 A | | 11/2016 | |
| JP | 2016200423 A | * | 12/2016 | |
| JP | 6675656 B1 | | 4/2020 | |
| WO | WO-2011116375 A1 | * | 9/2011 | ......... G01B 11/2513 |

* cited by examiner

FIG.7

| CORROSION GRADE | REINFORCEMENT BAR STATE |
|---|---|
| I | A BLACK COATED STATE, OR RUST DEVOLOPED BUT THIN FINE RUST OVERALL AND RUST NOT ADHERED TO CONCRETE SURFACE |
| II | LOCAL LOOSE RUST PRESENT AND MOTLED PATTERN ON SMALL SURFACE AREA |
| III | ALTHOUGH CROSS-SECTION DAMAGE NOT OBSERVABLE BY EYE, LOOSE RUST OCCURRING AROUND WHOLE CIRCUMFERENCE OR WHOLE LENGTH OF REINFORCEMENT BAR |
| IV | CROSS-SECTION DAMAGE OCCURRING |

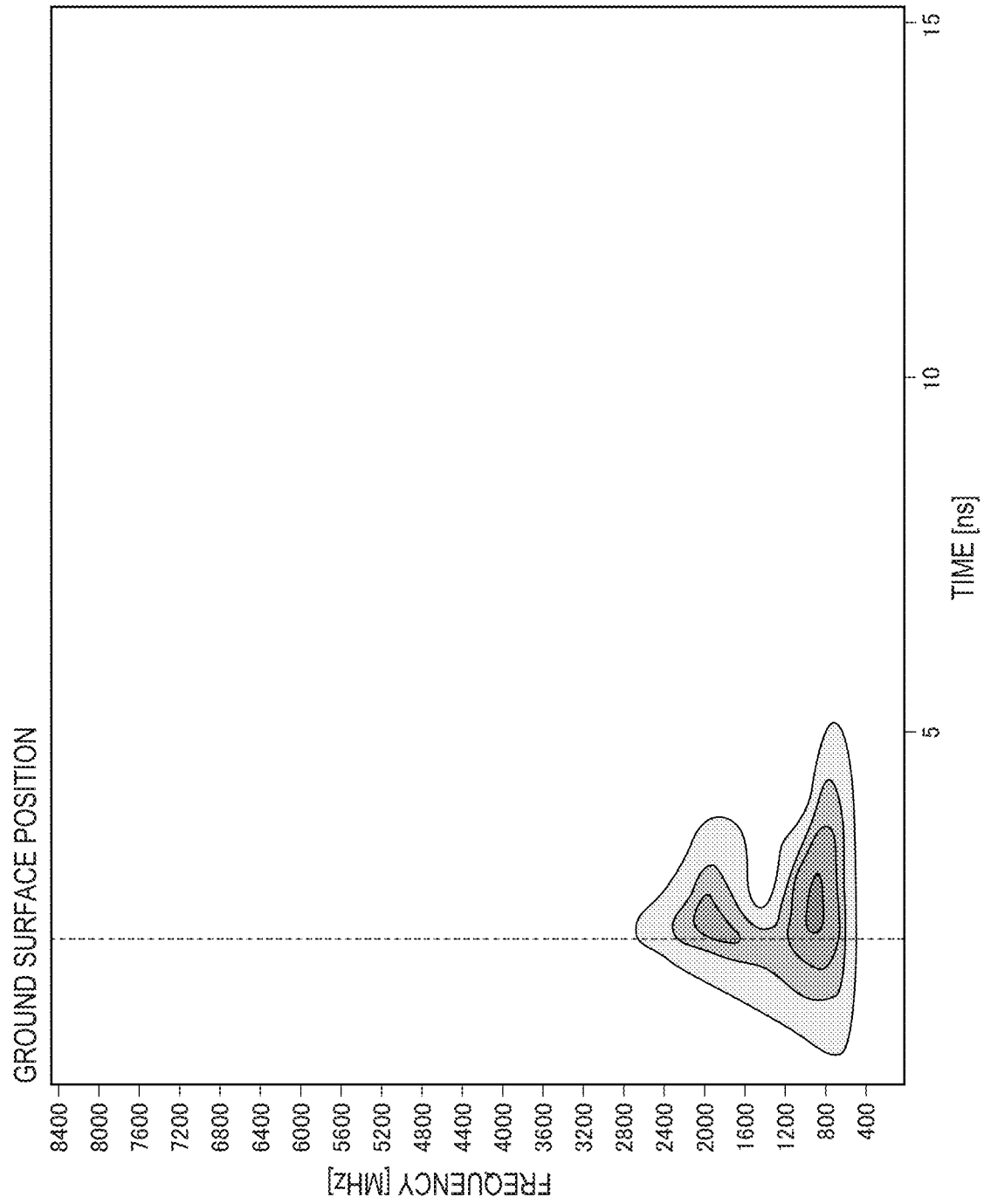

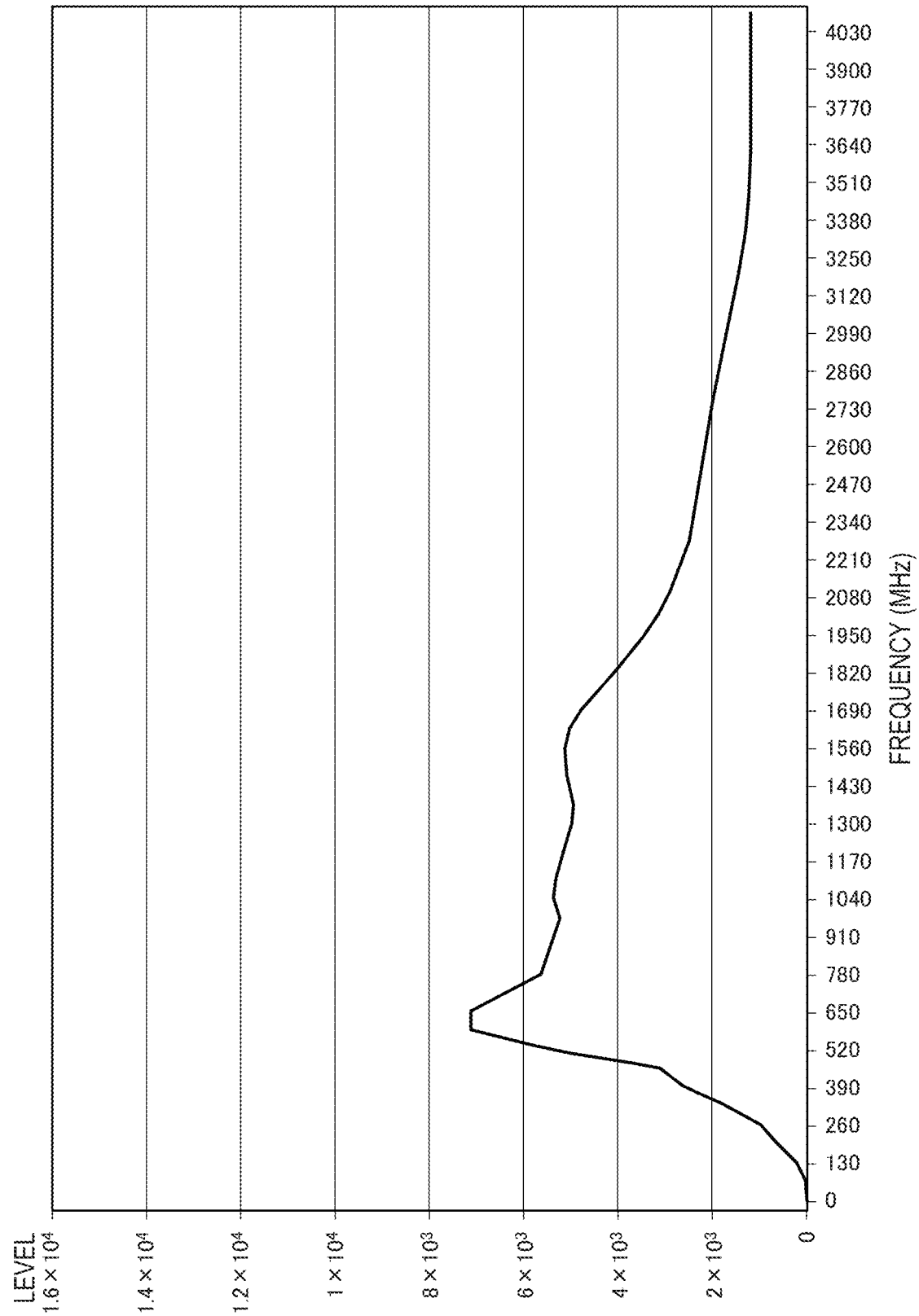

REINFORCEMENT BAR CORROSION EVALUATION DEVICE, REINFORCEMENT BAR CORROSION EVALUATION METHOD, AND COMPUTER PROGRAM

TECHNICAL FIELD

The present application claims priority from Japanese Patent Application No. 2019-210215 filed on Nov. 21, 2019, the disclosure of which is incorporated in its entirety by reference herein.

The present invention relates to a reinforcement bar corrosion evaluation device, a reinforcement bar corrosion evaluation method, and a computer program.

BACKGROUND ART

Reinforced concrete (RC) structures are configured mainly from concrete and reinforcement bar. Concrete is weak to tensile forces, and so the reinforcement bars bear these tensile forces and the concrete bears compressive forces. Thus there is a loss of load withstanding performance and durability of the RC structure when, accompanying changes with the passage of time, the concrete is no longer able to bear tensile forces or the reinforcement bar is no longer able to bear compressive forces. The purpose of a structural object is not able to be fulfilled when the required load withstanding performance and durability is lost, and so remedial works such as repair or reinforcement are normally undertaken, prior to the loss of the load withstanding performance and durability.

For example, in a RC deck bridge that employs reinforced concrete deck panels (RC deck panels), corrosion occurs in the reinforcement bar inside the RC deck panels due to changes with the passage of time etc. When such corrosion occurs in the reinforcement bar, there is a need to correctly evaluate the state of reinforcement bar corrosion so as not to lose the load withstanding performance and durability of the deck panels. However, correct evaluation of the load withstanding performance and durability of a RC deck bridge is not easy, and usually the evaluation of the in-service RC deck bridges is subjected to the non-destructive one and it makes the evaluation more difficult. Technology has been proposed to estimate the state of corrosion of reinforcement bar in RC deck bridges from various information.

For example, a reinforcement bar corrosion evaluation method is described in Japanese Patent Application Laid-Open (JP-A) No. 2016-191697 for reinforcement bar in reinforced concrete deck panels. This corrosion evaluation method includes a heating step in which a surface of an asphalt mixture paving the surface of reinforced concrete is heated by electromagnetic induction heating for a predetermined prescribed period of time, a temperature measurement step of measuring a temperature of the surface of the asphalt mixture and acquiring temperature information about changes to the asphalt surface with the passage of time, and a corrosion ratio calculation step of calculating a corrosion ratio of reinforcement bar inside concrete from a difference in a surface temperature of an asphalt mixture when reinforcement bar is in a non-corroded state and a surface temperature of an asphalt mixture for reinforcement bar in a corroded state that needs to be evaluated.

SUMMARY OF INVENTION

Technical Problem

However, in the invention disclosed in JP-A No. 2016-191697 there is a need to heat the surface of the asphalt mixture for a prescribed period of time, and the invention is not able to efficiently and quantitatively evaluate the degree of corrosion of the internal reinforcement bar. There is a desire to be able to efficiently and quantitatively evaluate the degree of corrosion of reinforcement bar inside RC deck panels non-destructively.

In consideration of the above circumstances, an object of the present invention is to provide a reinforcement bar corrosion evaluation device, a reinforcement bar corrosion evaluation method, and a computer program that are capable of efficiently and quantitatively evaluating the degree of corrosion of reinforcement bar in a reinforced concrete deck bridge non-destructively.

Solution to Problem

A reinforcement bar corrosion evaluation device according to a first aspect is a reinforcement bar corrosion evaluation device for evaluating a degree of corrosion of reinforcement bar in a reinforced concrete deck bridge. The reinforcement bar corrosion evaluation device includes an acquisition section configured to acquire reflection response data related to a reflection response of electromagnetic waves irradiated from a surface of the reinforced concrete deck bridge in a depth direction of the reinforced concrete deck bridge, a removal section configured to remove a surface frequency component obtained by the electromagnetic waves being reflected at the surface of the reinforced concrete deck bridge from a frequency distribution of a reflection response expressing the reflection response data acquired by the acquisition section, and an evaluation section configured to evaluate a degree of corrosion of the reinforcement bar in the reinforced concrete deck bridge by using a first measurement peak value in the frequency distribution of the reflection response from which the surface frequency component has been removed by the removal section, which is a peak value of a level of a frequency component of a first frequency band, and using a second measurement peak value therein, which is a peak value of a level of a frequency component of a second frequency band that is a higher frequency band than the first frequency band.

In a reinforcement bar corrosion evaluation device according to a second aspect, the removal section further removes a frequency component obtained for the electromagnetic waves reflected at the surface of the reinforced concrete deck bridge from the frequency distribution of the reflection response from which the surface frequency component has been removed.

In a reinforcement bar corrosion evaluation device according to a third aspect, the evaluation section compares the first measurement peak value and the second measurement peak value and evaluates the degree of corrosion of the reinforcement bar in the reinforced concrete deck bridge based on a magnitude relationship between the first measurement peak value and the second measurement peak value.

In a reinforcement bar corrosion evaluation device according to a fourth aspect, the evaluation section evaluates the degree of corrosion to be that corrosion of the reinforcement bar has progressed in the reinforced concrete deck bridge in a case in which the second measurement peak value is greater than the first measurement peak value.

In a reinforcement bar corrosion evaluation device according to a fifth aspect, the evaluation section uses, as a standard value, a peak value of a level of the first frequency band in a standard frequency distribution, which is a frequency distribution of a reflection response obtained by removing the frequency component from the reflection response obtained by irradiating electromagnetic waves against an un-deteriorated reinforced concrete deck bridge, and evaluates the degree of corrosion of the reinforcement bar in the reinforced concrete deck bridge by comparing the first measurement peak value against the standard value.

In a reinforcement bar corrosion evaluation device according to a sixth aspect, the evaluation section uses a prescribed proportion with respect to the standard value as a threshold, and evaluates the degree of corrosion as corrosion having progressed in the reinforcement bar in the reinforced concrete deck bridge in a case in which the first measurement peak value is less than the threshold.

In a reinforcement bar corrosion evaluation device according to a seventh aspect, the evaluation section evaluates the degree of corrosion of the reinforcement bar in the reinforced concrete deck bridge at plural positions on the surface of the reinforced concrete deck bridge.

A reinforcement bar corrosion evaluation method according to an eighth aspect is a reinforcement bar corrosion evaluation method for evaluating a degree of corrosion of reinforcement bar in a reinforced concrete deck bridge. The reinforcement bar corrosion evaluation method includes an acquisition step of acquiring reflection response data related to a reflection response of electromagnetic waves irradiated from a surface of the reinforced concrete deck bridge in a depth direction of the reinforced concrete deck bridge, a removal step of removing a surface frequency component obtained by the electromagnetic waves being reflected at the surface of the reinforced concrete deck bridge from a frequency distribution of a reflection response expressing the reflection response data acquired by the acquisition step, and an evaluation step of evaluating a degree of corrosion of the reinforcement bar in the reinforced concrete deck bridge by using a first measurement peak value in the frequency distribution of the reflection response from which the surface frequency component has been removed by the removal step, which is a peak value of a level of a frequency component of a first frequency band, and using a second measurement peak value therein, which is a peak value of a level of a frequency component of a second frequency band that is a higher frequency band than the first frequency band.

A reinforcement bar corrosion evaluation method according to a ninth aspect is a computer program for evaluating a degree of corrosion of reinforcement bar in a reinforced concrete deck bridge. The computer program causes a computer to execute processing including an acquisition step of acquiring reflection response data related to a reflection response of electromagnetic waves irradiated from a surface of the reinforced concrete deck bridge in a depth direction of the reinforced concrete deck bridge, a removal step of removing a surface frequency component obtained by the electromagnetic waves being reflected at the surface of the reinforced concrete deck bridge from a frequency distribution of a reflection response expressing the reflection response data acquired by the acquisition step, and an evaluation step of evaluating a degree of corrosion of the reinforcement bar in the reinforced concrete deck bridge by using a first measurement peak value in the frequency distribution of the reflection response from which the surface frequency component has been removed by the removal step, which is a peak value of a level of a frequency component of a first frequency band and using a second measurement peak value therein, which is a peak value of a level of a frequency component of a second frequency band that is a higher frequency band than the first frequency band.

Advantageous Effects

The present invention enables provision of a reinforcement bar corrosion evaluation device, a reinforcement bar corrosion evaluation method, and a computer program that are capable of efficiently and quantitatively evaluating the degree of corrosion of reinforcement bar in a reinforced concrete deck bridge non-destructively.

BRIEF DESCRIPTION OF DRAWINGS

FIG. 7 is a diagram illustrating relationships between corrosion grades and reinforcement bar states.

FIG. 8 is a diagram illustrating a time-frequency relationship.

FIG. 28 is a frequency distribution graph of the time-frequency distribution of FIG. 27 transformed into a frequency distribution.

DESCRIPTION OF EMBODIMENTS

Figure 1:
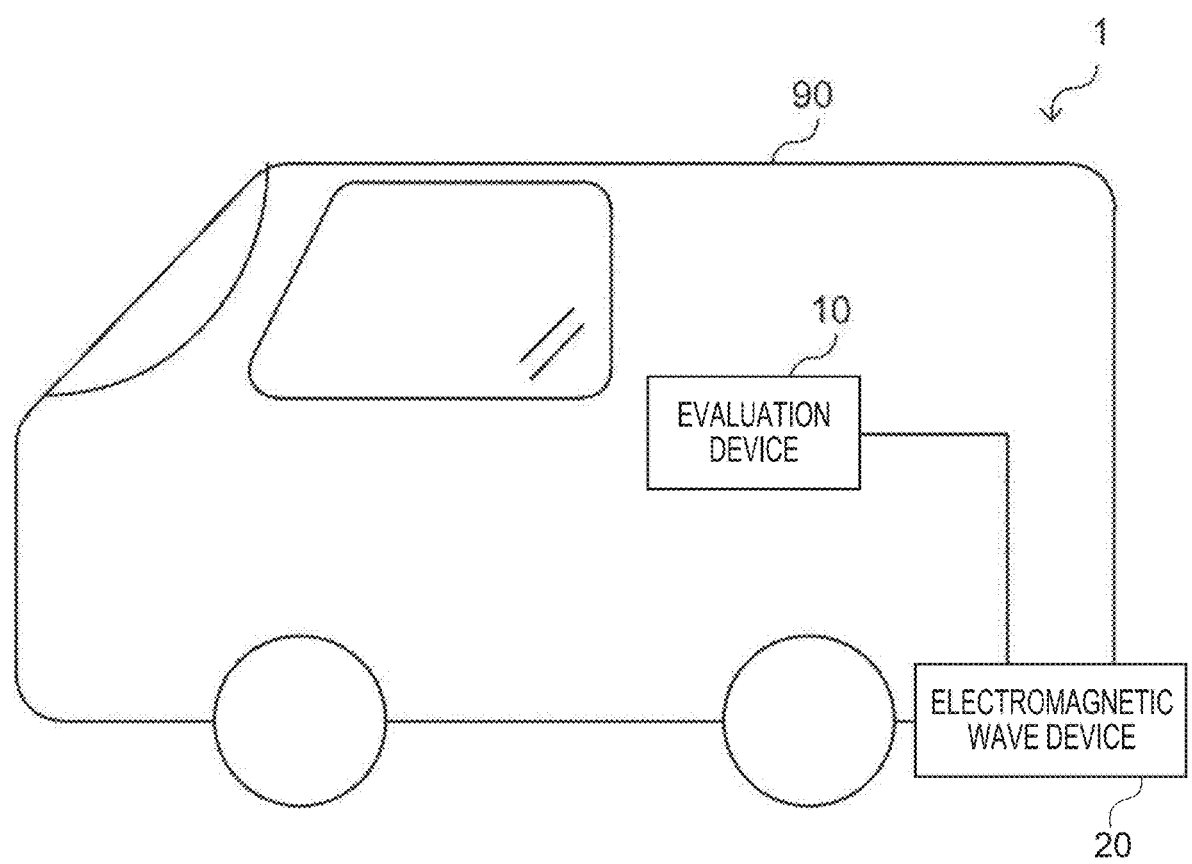
FIG. 1 is a schematic configuration diagram of a reinforcement bar corrosion evaluation system.

Explanation follows regarding an example of an exemplary embodiment of the present invention, with reference to the drawings. Note that the same reference numerals are appended to the same or equivalent configuration elements and portions in each of the drawings. Moreover, dimensional proportions in the drawings are sometimes exaggerated for ease of explanation and differ from actual proportions.

In the exemplary embodiment of the present invention a degree of corrosion is evaluated for reinforcement bar in a RC deck bridge, which is a road surface structural body of a road bridge or the like.

Figure 2:
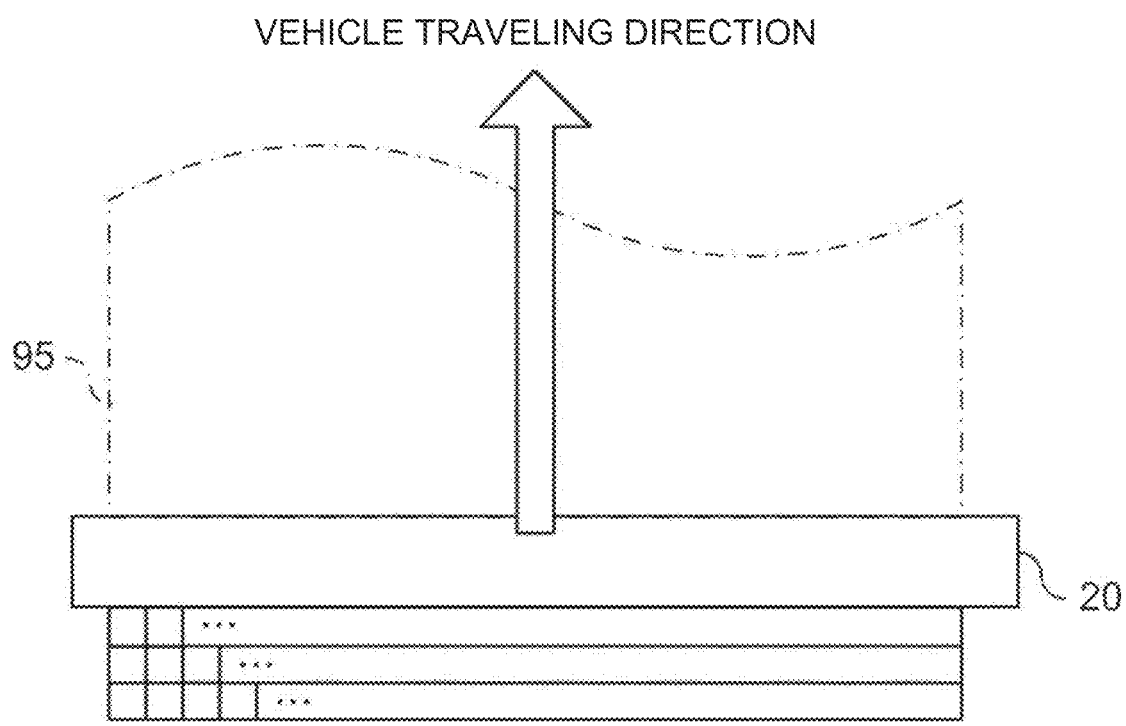
FIG. 2 is a diagram to explain detection of a reflection response waveform.
Figure 3:
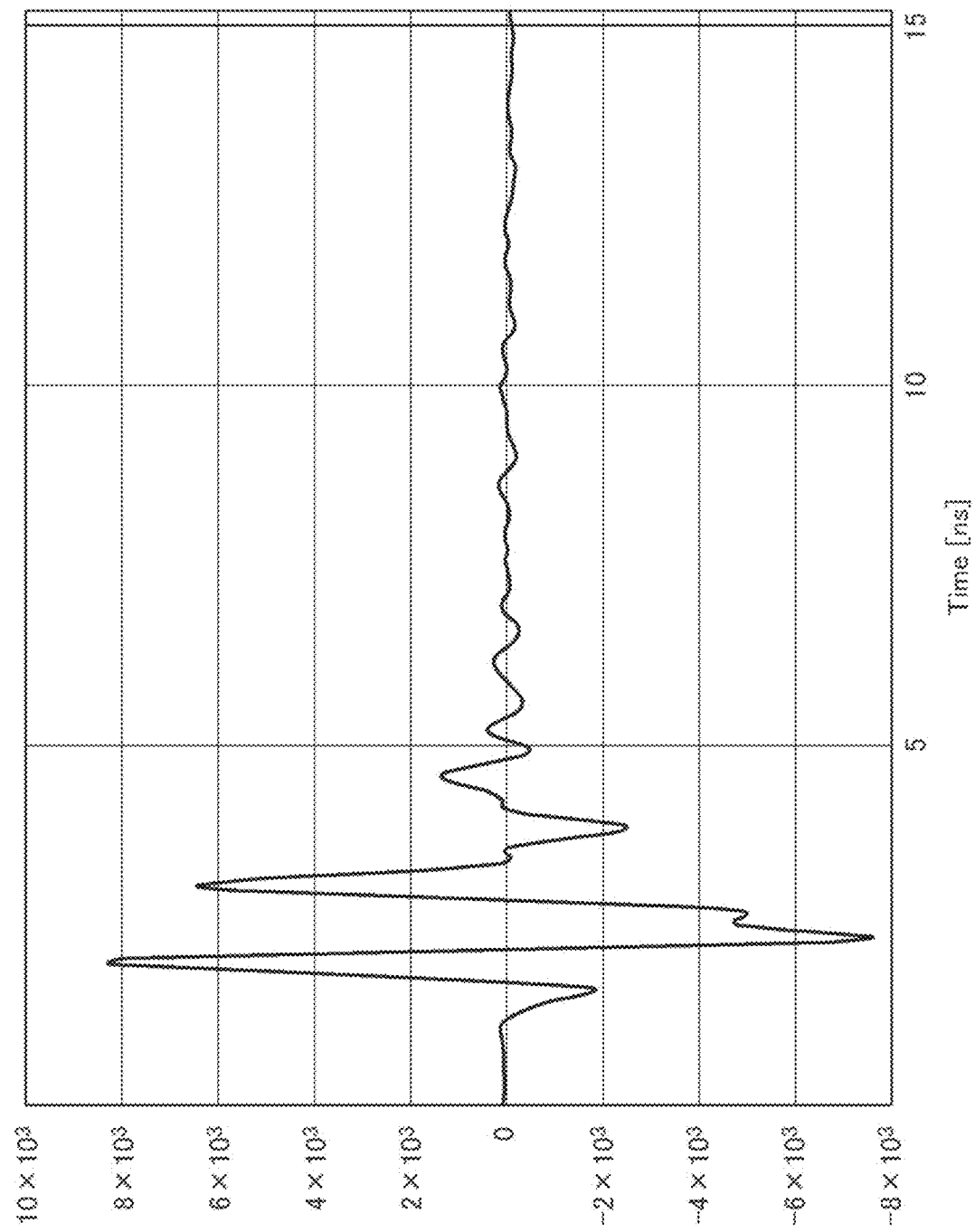
FIG. 3 is a diagram illustrating an example of a reflection response waveform detected for a single grid square.
Figure 4:
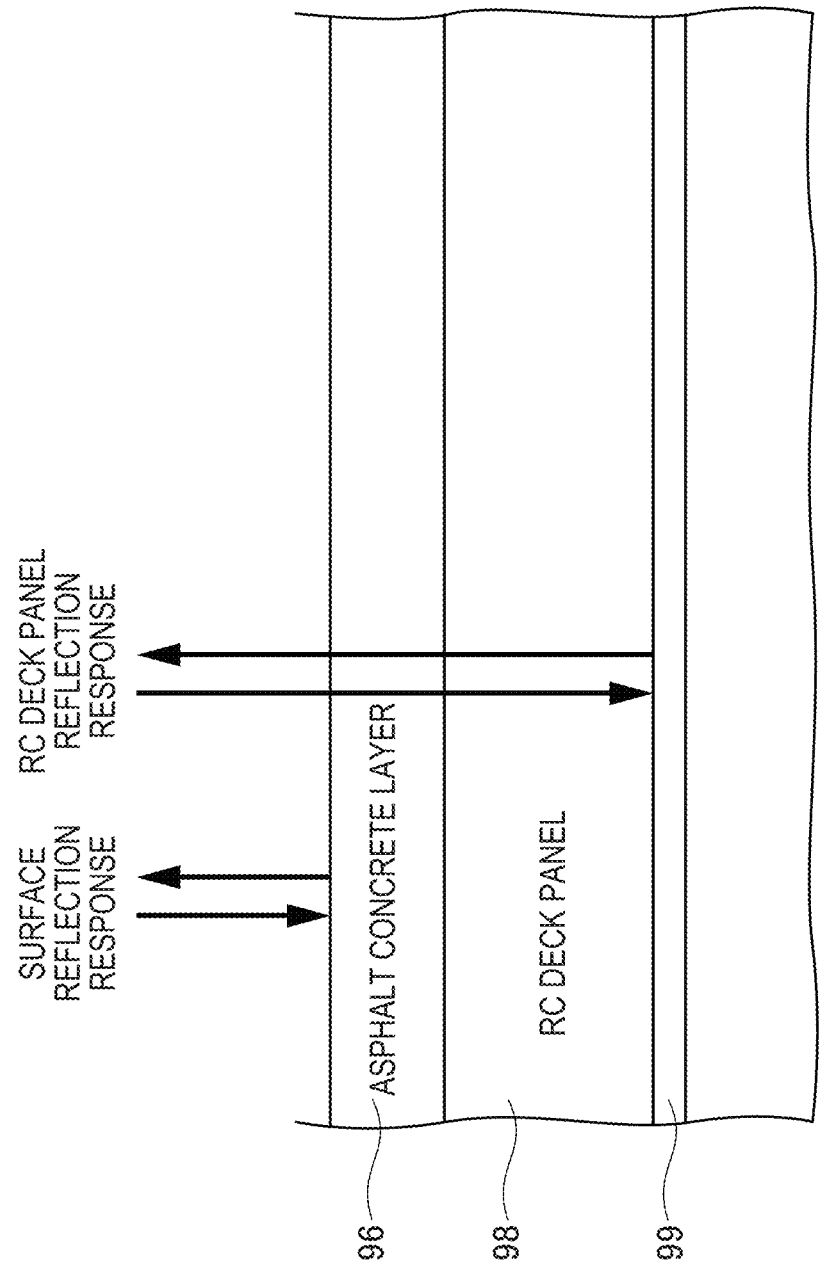
FIG. 4 is a cross-section illustrating a schematic cross-section of a RC deck bridge.

FIG. 1 is a schematic configuration diagram of a reinforcement bar corrosion evaluation system. FIG. 2 is a diagram to explain detection of a reflection response waveform. FIG. 3 is a diagram illustrating an example of a reflection response waveform detected in a single grid square. FIG. 4 is a cross-section illustrating a schematic cross-section of a RC deck bridge.

As illustrated in FIG. 1, a reinforcement bar corrosion evaluation system 1 according to the present exemplary embodiment is mounted to a vehicle 90.

The reinforcement bar corrosion evaluation system 1 is configured including a reinforcement bar corrosion evaluation device 10 and an electromagnetic wave device 20. The reinforcement bar corrosion evaluation device 10 is a device for evaluating the degree of corrosion of reinforcement bar, and in particular upper reinforcement bar, of a RC deck bridge in which RC deck panels are buried below asphalt. Details are described later regarding the reinforcement bar corrosion evaluation device 10. In the following the reinforcement bar corrosion evaluation system 1 will simply be referred to as evaluation system 1, and the reinforcement bar corrosion evaluation device 10 will simply be referred to as evaluation device 10. Similar applies to the drawings.

The electromagnetic wave device 20 includes plural electromagnetic wave transmitters and receivers provided along a line. The electromagnetic wave device 20 is provided to a lower rear portion of the vehicle 90, for example, such that the traveling direction of the vehicle 90 is along the bridge axis direction, and the line direction of the electromagnetic wave device 20 is in a direction at right angles to the bridge axis. The electromagnetic wave transmitters transmit electromagnetic waves such as microwaves or the like toward the RC deck bridge. The receivers receive reflection waves reflected by each section of the RC deck bridge.

A known electromagnetic wave radar system may be employed without particular limitation as the electromagnetic wave transmitter, however a radar system with many transceiver sensors arranged side-by-side is preferably employed therefor from the perspectives of work efficiency and accuracy. Array antennas that are arranged in the array pattern are preferably provided as the transceiver sensors from the perspective of work efficiency.

Impulse transmission may be employed as the sensors employed in the radar system, and impulse transmission with a center range in a frequency of from 0.5 GHz to 3 GHz are preferably employed for evaluating the degree of corrosion of reinforcement bar of an RC deck bridge. In particular, the survey with the center frequency which is higher than 1 GHz makes waveform length shorter and improves the measurement resolution.

As illustrated in FIG. 2, the electromagnetic wave device 20 transmits electromagnetic waves through the surface in a direction (depth direction) into the interior of the RC deck bridge and receives reflection waves therefrom while scanning an evaluation target range 95 on the RC deck bridge surface in the vehicle traveling direction. Reflection wave intensities are thus detected according to depth for each respective grid square of the evaluation target range 95. The reflection wave intensities according to depth are detected by the shape of a reflection response waveform for each of the grid squares, as illustrated in FIG. 3. As an example, each grid square may be set at 1 cm×1 cm and the width of a single line at 2.0 m. In such a configuration, reflection response waveforms are detected for 200 grid squares in a single line.

The depth corresponds to the amount of time between transmitting electromagnetic waves from the electromagnetic wave device 20 and receiving the reflection waves with the electromagnetic wave device 20. A reflection wave intensity for each depth of the RC deck bridge can be obtained by extracting a reflection wave intensity corresponding to each desired depth from the reflection response waveform as illustrated in FIG. 3.

The electromagnetic wave device 20 outputs information to the evaluation device 10 about the reflection response waveform (the reflection wave intensity according to depth) acquired for each of the grid squares. Note that the electromagnetic wave device 20 is not limited to a mode attached to the vehicle 90, and another mode may be employed, such as a mode held by a worker, a handcart mode, or the like.

As illustrated in FIG. 4, the RC deck bridge is formed by stacked layers of an asphalt concrete layer 96 and an RC deck panel 98. The RC deck panel 98 is a deck panel configured by burying plural reinforcement bar 99 in concrete. The electromagnetic waves irradiated from the electromagnetic wave device 20 are reflected with respective time differences at the asphalt concrete layer 96 and at the RC deck panel 98. Thus the reflection response from the RC deck bridge includes a surface reflection response reflected at the asphalt concrete layer 96, and an RC deck panel reflection response reflected at the reinforcement bar 99 inside the RC deck panel 98. These reflection responses may be expressed as a reflection response waveform as illustrated in FIG. 3. Note that the RC deck bridge is not necessarily always a bridge, and any structural body may be employed therefore as long as it is a road structural body including a structure such as described above.

Figure 5:
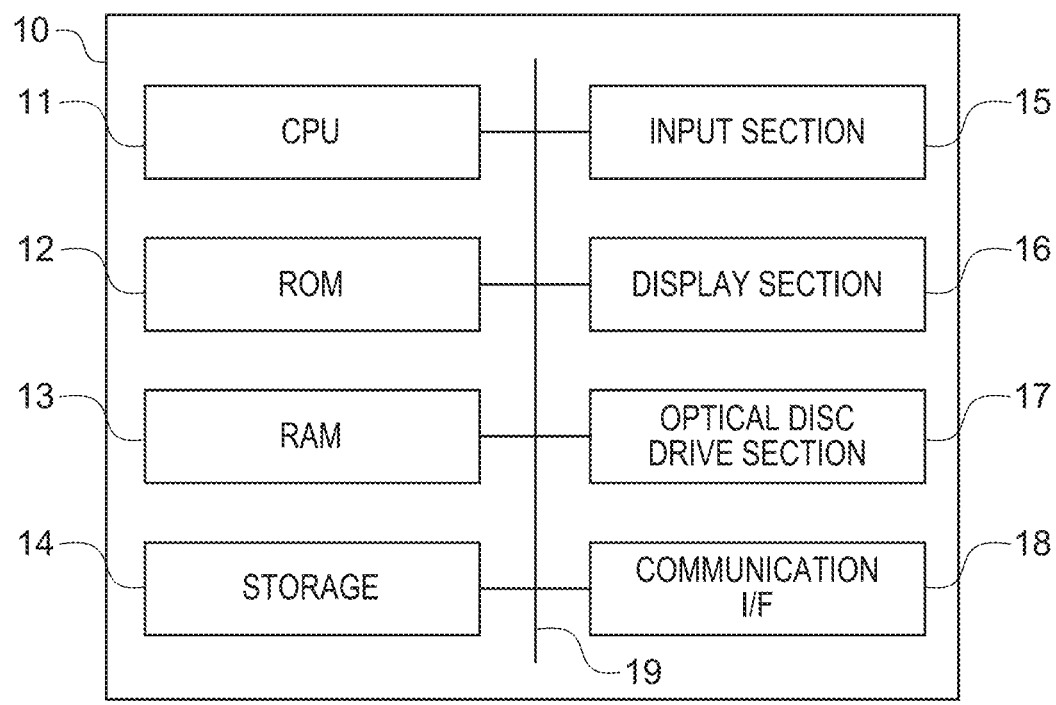
FIG. 5 is a block diagram illustrating a hardware configuration of an evaluation device.

FIG. 5 is a block diagram illustrating a hardware configuration of the evaluation device.

As illustrated in FIG. 5, the evaluation device 10 includes configuration of a central processing unit (CPU) 11, read only memory (ROM) 12, random access memory (RAM) 13, storage 14, an input section 15, a display section 16, an optical disc drive section 17, and a communication interface (communication I/F) 18. The respective configurations are connected so as to be capable of communicating with each other through a bus 19.

The CPU 11 is a central processing unit that executes various programs and controls various sections. Namely, the CPU 11 reads a program from the ROM 12 or the storage 14, and executes the program using the RAM 13 as a workspace. The CPU 11 controls respective configurations and performs various arithmetic processing according to the program recorded in the ROM 12 or the storage 14. In the present exemplary embodiment, an evaluation program for evaluating the degree of corrosion of reinforcement bar in a RC deck bridge (reinforcement bar corrosion evaluation program) is stored in the ROM 12 or the storage 14.

The ROM 12 holds various programs and various data. The RAM 13 acts as a workspace to temporarily store programs or data. The storage 14 is configured by a hard disk drive (HDD) or a solid state drive (SSD), and is stored with various programs including an operating system, as well as various data.

The input section 15 includes a keyboard and a pointing device such as a mouse, and is used to perform various input. The display section 16 is for example a liquid crystal display used to display various information. The display section 16 may take the form of a touch panel and thereby also function as the input section 15.

The optical disc drive section 17 reads data stored on various recording media such as compact disc read only memory (CD-ROM) or Blu-Ray discs, and also writes data to such recording media.

The communication interface 18 is an interface to communicate with other equipment and employs, for example, a standard such as Ethernet (registered trademark), FDDI, or Wi-Fi (registered trademark).

Next, explanation follows regarding a functional configuration of the evaluation device 10.

Figure 6:
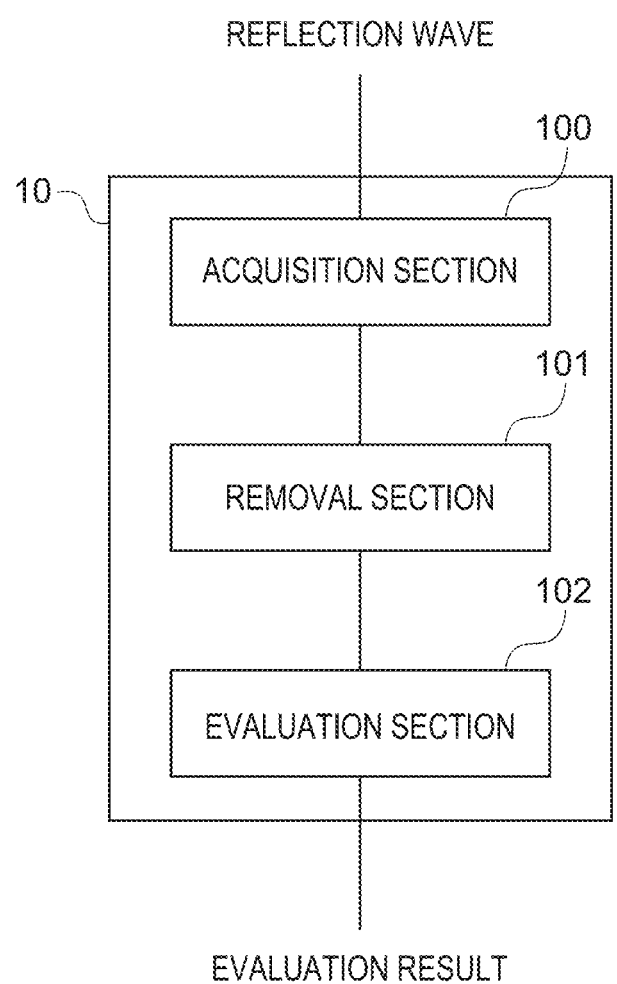
FIG. 6 is a block diagram illustrating an example of a functional configuration of an evaluation device.

FIG. 6 is a block diagram illustrating an example of functional configuration of the evaluation device 10.

As illustrated in FIG. 6, the evaluation device 10 includes an acquisition section 100, a removal section 101, and an evaluation section 102 as functional configurations. Each of these functional configurations is implemented by the CPU 11 reading the reinforcement bar corrosion evaluation program stored in the ROM 12 or the storage 14, and expanding and executing the evaluation program in the RAM 13.

The acquisition section 100 acquires reflection response data relating to the reflection response to the electromagnetic waves irradiated through the surface of the RC deck bridge in the depth direction of the RC deck bridge. The acquisition section 100 acquires this reflection response data from the electromagnetic wave device 20.

A removal section 101 removes surface frequency components obtained by electromagnetic wave reflected at the surface of the RC deck bridge from out of the reflection response frequency distribution expressing the reflection response data acquired by the acquisition section 100. The surface frequency components are frequency components of reflection obtained in the vicinity of the surface of the RC deck panel pavement (a range including the asphalt concrete layer 96, and the interface between the asphalt concrete layer 96 and the RC deck panel 98), as expressed by the surface reflection response illustrated in FIG. 4.

The evaluation section 102 employs a first measurement peak value and a second measurement peak value to evaluate the degree of corrosion of reinforcement bar in the RC deck bridge. The first measurement peak value is a peak value of a level of frequency components in a first frequency band in the reflection response frequency distribution after the surface frequency components have been removed by the removal section 101. The second peak value is a peak value of a level of frequency components in a second frequency band, which is a higher frequency band than the first frequency band, in the reflection response frequency distribution after the surface frequency components have been removed by the removal section 101. An evaluation result of the evaluation section 102 is, for example, displayed on the display section 16.

The first frequency band is, for example, a band from 600 MHz to 800 MHz, and the second frequency band is, for example, a band from 1200 MHz to 1600 MHz.

The degree of corrosion of reinforcement bar is evaluated according to a standard called corrosion grade. FIG. 7 is a diagram illustrating relationships between corrosion grades and reinforcement bar states. The evaluation device 10 evaluates which, from out of the corrosion grades illustrated in FIG. 7, is the corrosion grade of the reinforcement bar of the RC deck bridge being evaluated. Thus the evaluation result of the evaluation section 102 contains information of which corrosion grade applies to which location on the RC deck bridge. Note that although the corrosion grades are expressed by Roman numerals in FIG. 7, the corrosion grades are expressed by Arabic numerals in the following explanation.

Next, description follows regarding removal of the surface frequency components by the removal section 101. In the evaluation device 10 according to the present exemplary embodiment, the degree of corrosion of reinforcement bar is evaluated by performing analysis to specific depth using time-frequency analysis.

There is a need to present the frequency components of the time positions in an easily understood format in order to perform analysis to specific depth using time-frequency analysis. For example, since the signal intensity is high for reflection waves at the vicinity of the surface, the level of these frequency components is high, and small frequency changes in the reflection waves from inside the RC deck panel 98 are not easily discerned. Thus in the evaluation device 10 according to the present exemplary embodiment, the frequency components for the vicinity of the surface, which have a high level and are not needed for analysis, are removed by the removal section 101. In the evaluation device 10 according to the present exemplary embodiment, the removal section 101 removes the frequency components for the surface vicinity, thereby enabling time-frequency analysis to be performed using the reflection waves from the interior of the RC deck panel 98.

In the evaluation device 10 according to the present exemplary embodiment, the subtraction of the surface vicinity frequency components of the reflection response data is repeated twice by the removal section 101. Repeating the subtraction of the surface vicinity frequency components twice in the evaluation device 10 according to the present exemplary embodiment is able to raise the reliability of the evaluation employing the internal frequency components to express the RC deck panel reflection response. A case in which the subtraction of the surface vicinity frequency components is performed only once is described later, as a comparative example to the case in which the subtraction is performed twice.

In the evaluation device 10 according to the present exemplary embodiment the time-frequency distribution of the internal frequency components is also transformed into a frequency distribution. The transformation from a time-frequency distribution to a frequency distribution may, for example, be executed by the evaluation section 102. The evaluation device 10 finds the first measurement peak value and the second measurement peak value described above from the frequency distribution of the internal frequency components. The evaluation device 10 employs the first measurement peak value and the second measurement peak value to evaluate the degree of corrosion of the reinforcement bar in the RC deck bridge.

In the evaluation device 10 according to the present exemplary embodiment, the electromagnetic waves are irradiated in advance onto a healthy RC deck bridge without reinforcement bar corrosion, and the surface vicinity frequency components are subtracted from the reflection waves from the RC deck bridge to derive a frequency distribution. This frequency distribution data of the healthy RC deck bridge is, for example, saved in the storage 14. The evaluation section 102 compares the data of the frequency distribution obtained by transmitting electromagnetic waves onto a RC deck bridge against the data of the frequency distribution for the healthy RC deck bridge to first determine whether or not there is corrosion in the reinforcement bar the RC deck bridge. When the evaluation section 102 has determined there to be corrosion in the reinforcement bar inside the RC deck panels, the corrosion grade of the reinforcement bar is then determined based on the data of the frequency distribution being evaluated.

Figure 9:
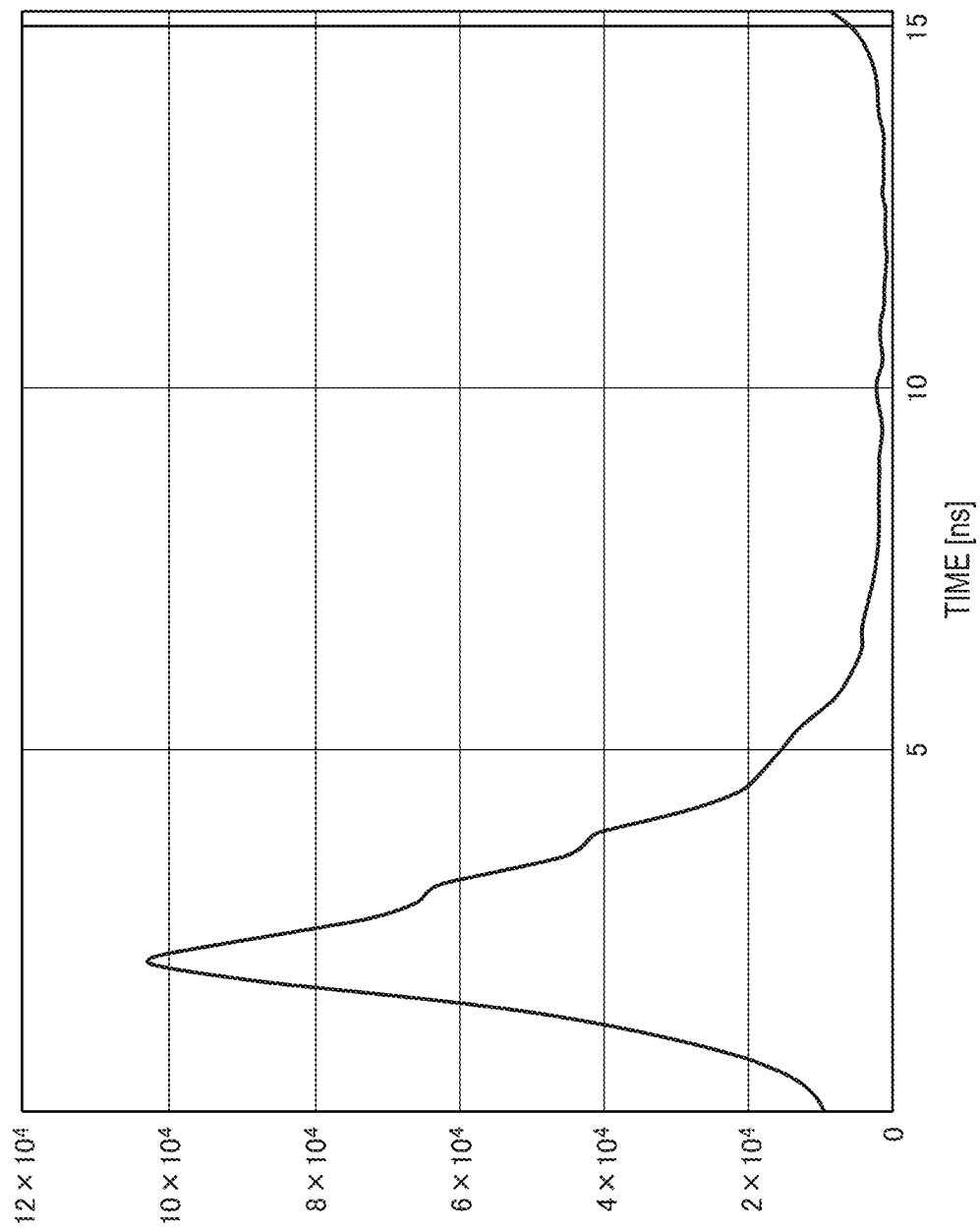
FIG. 9 is a diagram in which a surface vicinity frequency component has been extracted from reflection response data.
Figure 10:
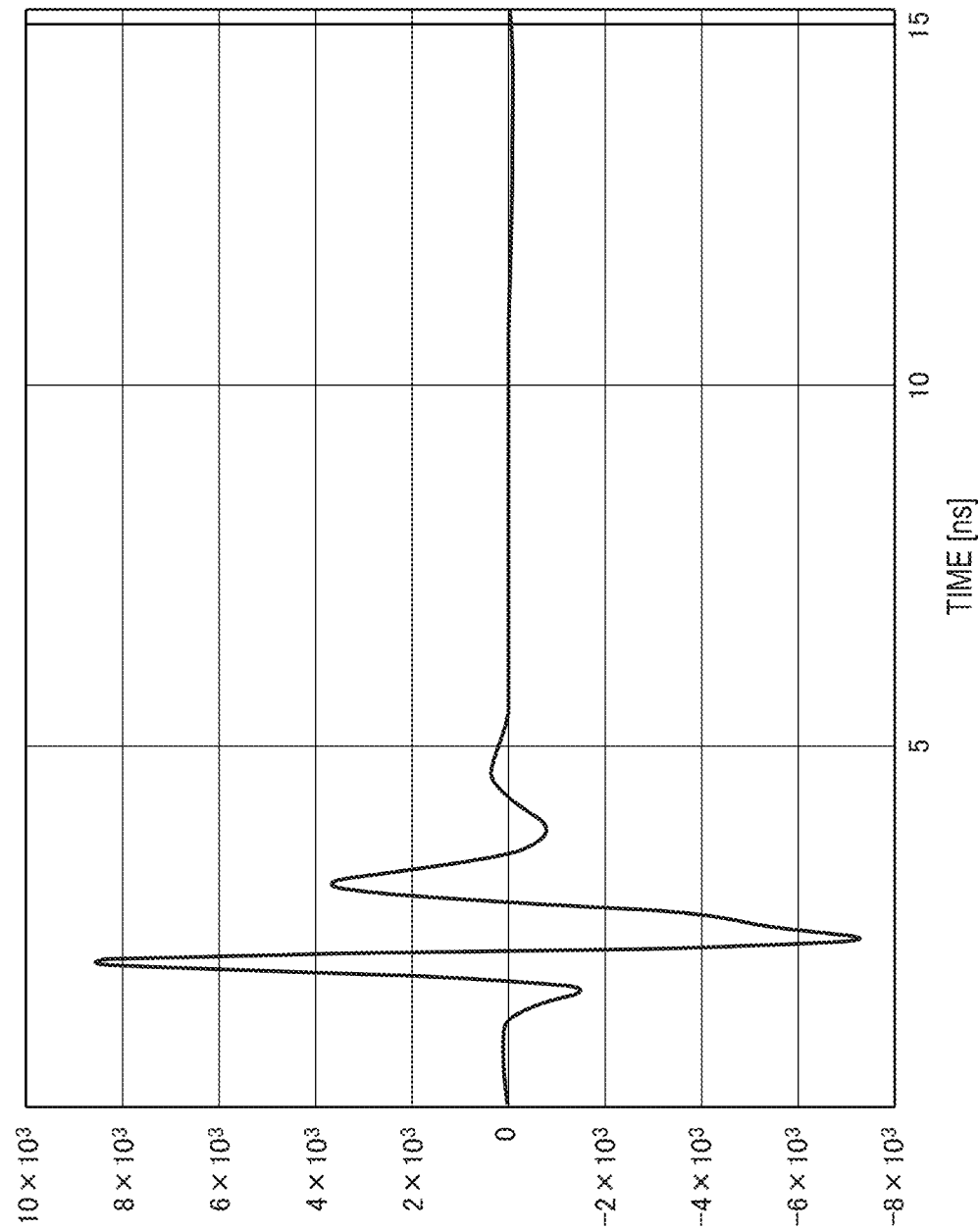
FIG. 10 is a diagram of frequency components transformed into a time domain waveform by inverse FFT.
Figure 11:
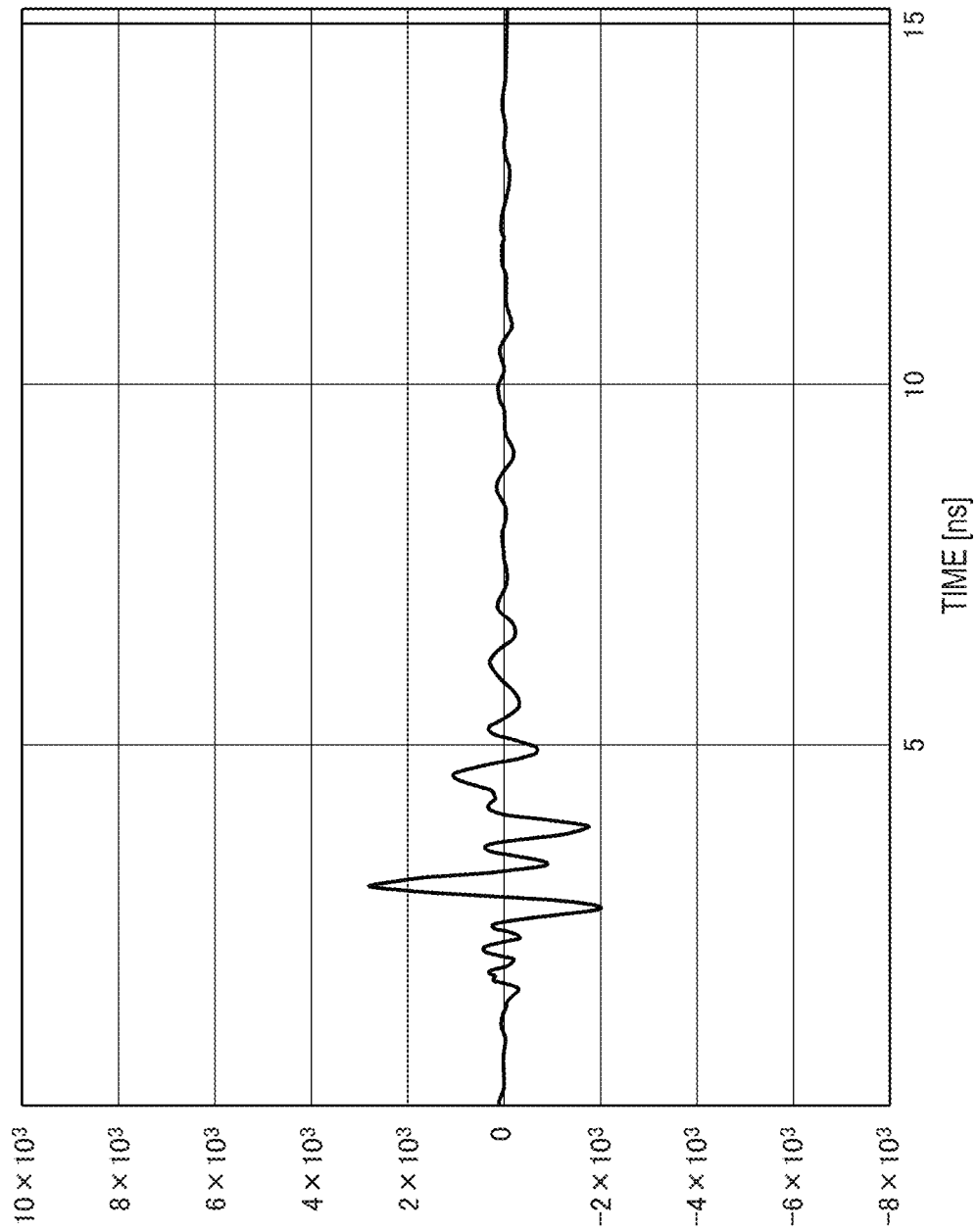
FIG. 11 is a diagram of the waveform illustrated in FIG. 10 subtracted from the reflection response illustrated in FIG. 8.
Figure 12:
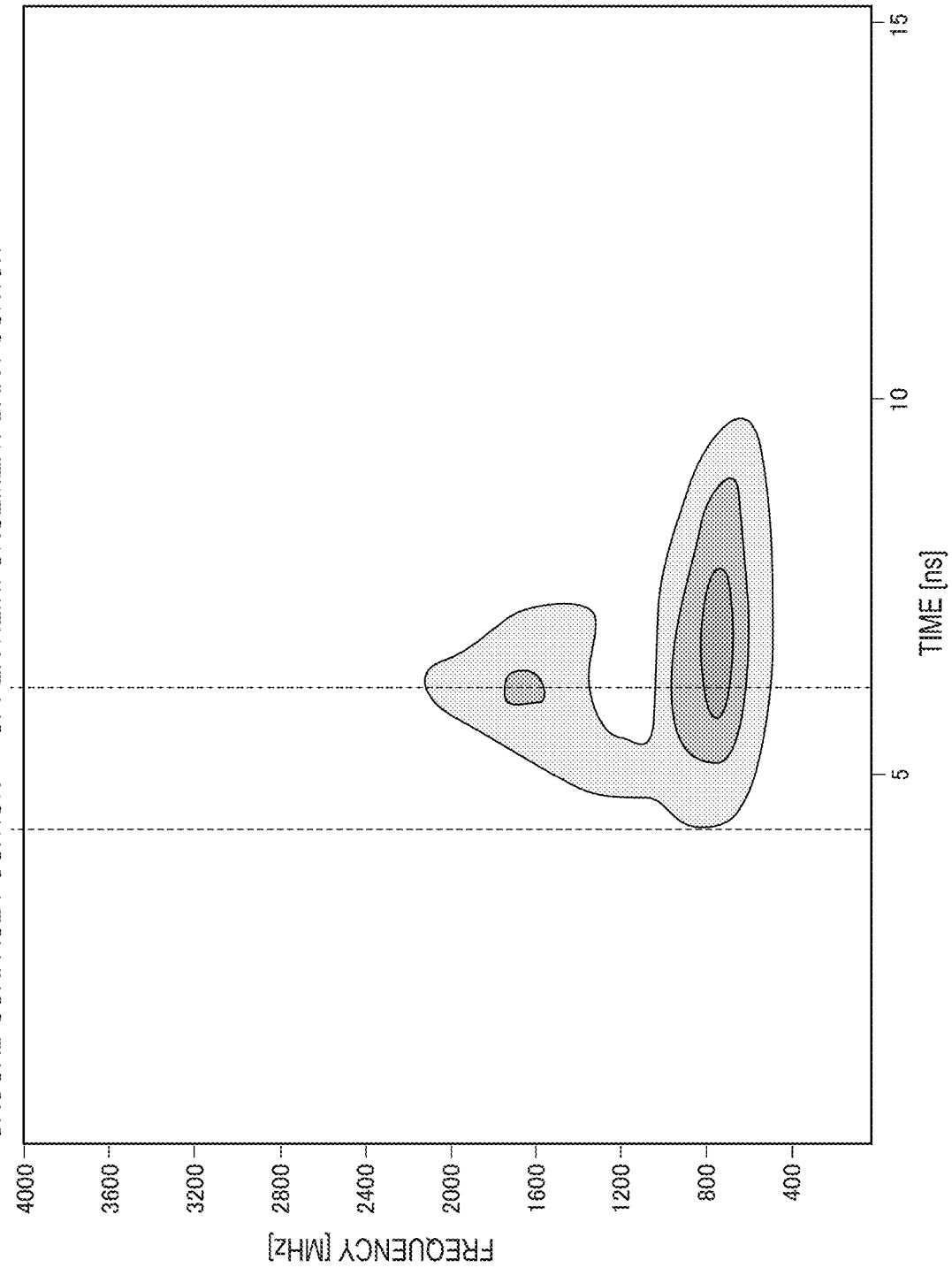
FIG. 12 is a time-frequency distribution graph illustrating a time-frequency relationship of the waveform illustrated in FIG. 11 expressed by an S transform.
Figure 13:
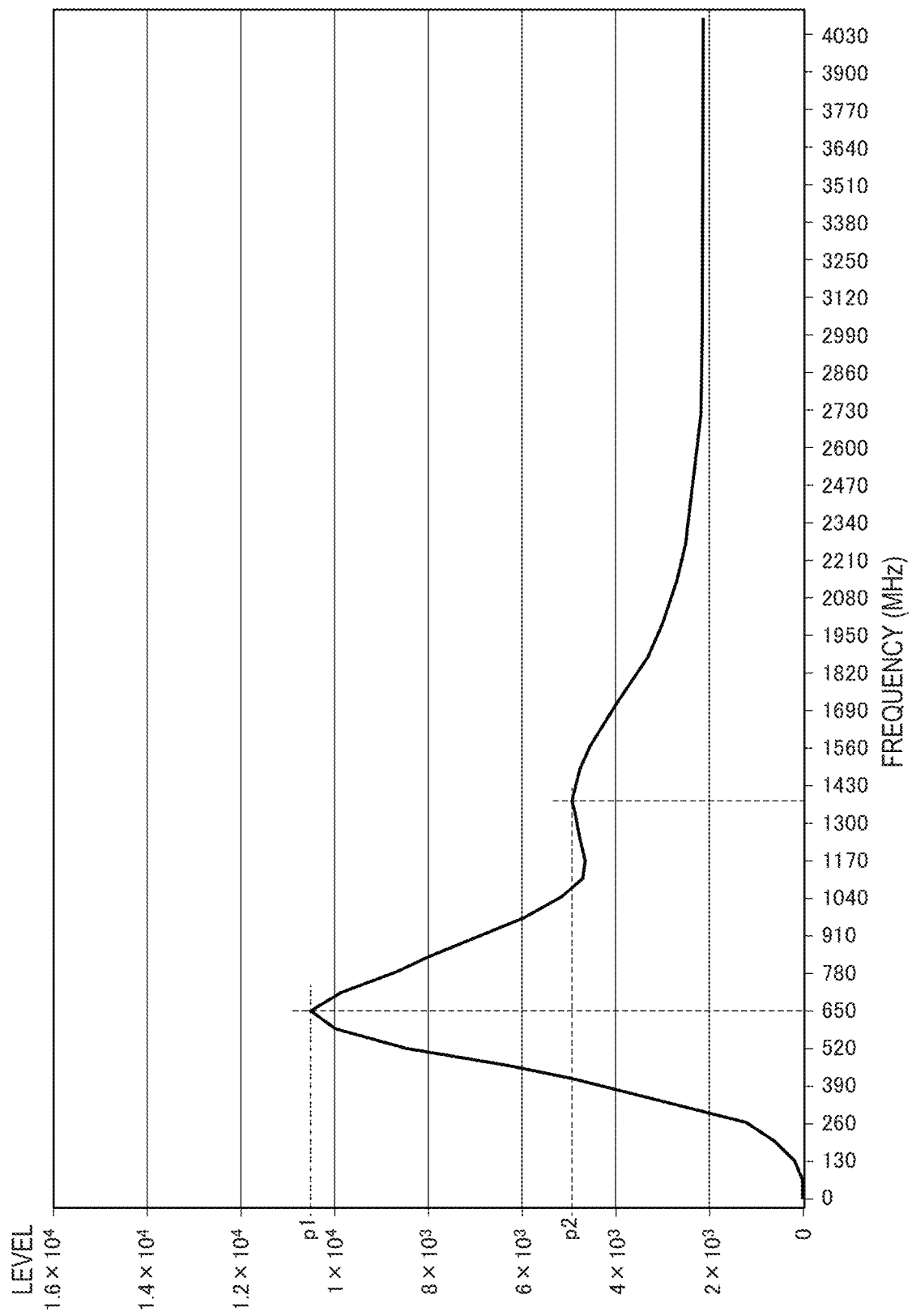
FIG. 13 is a frequency distribution graph of the time-frequency distribution of FIG. 12 transformed into a frequency distribution.

FIG. 8 is a time-frequency distribution graph illustrating a time-frequency relationship as expressed by a contour plot, by expressing the reflection response illustrated in FIG. 3 using an S Transform (S Transform: a time-frequency analysis method proposed by R. G. Stockwell). FIG. 9 is a diagram in which a surface vicinity frequency component has been extracted from the reflection response data. FIG. 10 is a graph illustrating the frequency components illustrated in FIG. 9 transformed into a time domain waveform using an inverse fast Fourier transform (FFT). FIG. 11 is a diagram illustrating the waveform obtained by subtracting the waveform illustrated in FIG. 10 from the reflection response illustrated in FIG. 3. FIG. 12 is a time-frequency distribution graph illustrating a contour plot of a time-frequency relationship for the waveform illustrated in FIG. 11 expressed by an S Transform. FIG. 13 is a frequency distribution graph obtained by transforming the time-frequency distribution illustrated in FIG. 12 to frequency distribution. The frequency distribution is obtained by combining all time regions. The diagrams illustrated by FIG. 8 to FIG. 13 are of characteristics obtained by transmitting electromagnetic waves onto the healthy RC deck bridge with no reinforcement bar corrosion.

In FIG. 3, FIG. 10, and FIG. 11 time is expressed on the horizontal axis, and a signal intensity of electromagnetic waves received is expressed on the vertical axis. In FIG. 8 and FIG. 12 time is expressed on the horizontal axis and frequency is expressed on the vertical axis. In FIG. 13 frequency is expressed on the horizontal axis and signal intensity is expressed on the vertical axis. In FIG. 8 and FIG. 12 the signal intensity is expressed in a grayscale. In FIG. 8 and FIG. 12 the stronger the signal intensity the darker the representation thereof. In FIG. 3 and in FIG. 8 to FIG. 12 time is expressed on the horizontal axis, however the time on the horizontal axis is the time of receipt of electromagnetic waves reflected by the RC deck bridge. The deeper the location in the RC deck bridge where the electromagnetic waves are reflected, the later the electromagnetic waves are received by the electromagnetic wave device 20, and so the horizontal axis of FIG. 3 and in FIG. 8 to FIG. 12 may be said to express a depth position in the vertical direction of the RC deck bridge.

The acquisition section 100 obtains waveforms of reflection response such as that illustrated in FIG. 3 from reflection response data acquired from the electromagnetic wave device 20. When the reflection response waveform illustrated in FIG. 3 is expressed by an S Transform, a time-frequency distribution graph such as that illustrated in FIG. 8 is obtained.

The time-frequency distribution graph illustrated in FIG. 8 includes surface frequency components representing the surface reflection response illustrated in FIG. 4, and internal frequency components representing the RC deck panel reflection response illustrated in FIG. 4. A waveform such as that illustrated in FIG. 11 results from removing the surface frequency components from the waveform of FIG. 3 using the removal section 101 as described above. Furthermore, the time-frequency distribution graph illustrated in FIG. 12 is obtained when the waveform illustrated in FIG. 11 is expressed by an S Transform. The time-frequency distribution graph illustrated in FIG. 12 does not contain the surface frequency components representing the surface reflection response illustrated in FIG. 4, but contains the internal frequency components representing the RC deck panel reflection response illustrated in FIG. 4. Thus a distribution that was buried in the frequency components of the reflection waves at the surface vicinity appears in the time-frequency distribution graph illustrated in FIG. 12.

The surface frequency components have a high reflection intensity of electromagnetic waves, and impart a large influence to the display of a frequency distribution on a time-frequency distribution graph. Thus removing the surface frequency components enables the internal frequency components representing the RC deck panel reflection response to be brought out into relief.

The signal intensity of each frequency is illustrated in the frequency distribution graph illustrated in FIG. 13. The evaluation section 102 employs a first measurement peak value p1 in the first frequency band in the frequency distribution graph and a second measurement peak value p2 in the second frequency band therein to evaluate the degree of corrosion of the reinforcement bar in the RC deck bridge.

In the present exemplary embodiment the evaluation section 102 evaluates the degree of corrosion of reinforcement bar by determining a corrosion grade of the reinforcement bar according to the following evaluation standard.

First, the evaluation section 102 determines whether or not the first measurement peak value is reduced by a prescribed threshold or greater, for example 50% or greater, with respect to the first measurement peak value in the frequency distribution data of the healthy RC deck bridge. It is thought that as the corrosion of reinforcement bar inside the RC deck panels progresses, the intensity of the reflection waves from the reinforcement bar falls in response to the electromagnetic waves irradiated from the electromagnetic wave device 20. Thus the evaluation section 102 employs the amount of fall, with respect to the first measurement peak value in the frequency distribution data of the healthy RC deck bridge, in the determination standard for the presence/absence of progression in reinforcement bar corrosion.

The evaluation section 102 determines that the reinforcement bar being evaluated is corrosion grade 1 unless the first measurement peak value is reduced by the prescribed threshold or greater from the first measurement peak value of the frequency distribution data of the healthy RC deck bridge. In contrast, the evaluation section 102 determines that the reinforcement bar being evaluated is a corrosion grade from 2 to 4 when the first measurement peak value is reduced by the prescribed threshold or greater from the first measurement peak value of the frequency distribution data of the healthy RC deck bridge.

Then the evaluation section 102 compares the magnitude relationship between the first measurement peak value and the second measurement peak value. The evaluation section 102 determines the reinforcement bar being evaluated to be either corrosion grade 2 or 3 when the first measurement peak value is greater than the second measurement peak value. In contrast, the evaluation section 102 determines the reinforcement bar being evaluated to be corrosion grade 4 when the second measurement peak value is greater than the first measurement peak value.

In other words, for the corrosion grades 1, 2, or 3 the second frequency band component is not contained in the RC deck panel reflection response by as much as the first frequency band component, and for the corrosion grade 4 the second frequency band component is contained more in the RC deck panel reflection response than the first frequency band component. This phenomenon is thought to be caused by progression in the reinforcement bar corrosion. Thus the evaluation section 102 is able to evaluate the degree of progression in the reinforcement bar corrosion by comparing the magnitude relationship between the first measurement peak value and the second measurement peak value. The evaluation section 102 is able to evaluate that the reinforcement bar corrosion has progressed and the degree of progression of corrosion in cases in which the second measurement peak value is greater than the first measurement peak value.

The evaluation section 102 employs the first measurement peak value of the first frequency band in the frequency distribution of the internal frequency components and the second measurement peak value in the second frequency band therein to enable a quantitative evaluation of the degree of corrosion of the reinforcement bar in the RC deck bridge.

Note that although in the present exemplary embodiment the frequency distribution was obtained by combining all of the time regions, the present invention is not limited to such an example. Unwanted components for positions deeper than the reinforcement bar vicinity may be removed to obtain more distinct characteristics and, for example, the frequency component for time positions from the ground surface to the reinforcement bar vicinity may be extracted, and a frequency distribution found for the time regions limited to from the ground surface to the reinforcement bar vicinity.

Next, description follows regarding operation of the evaluation device 10.

Figure 14:
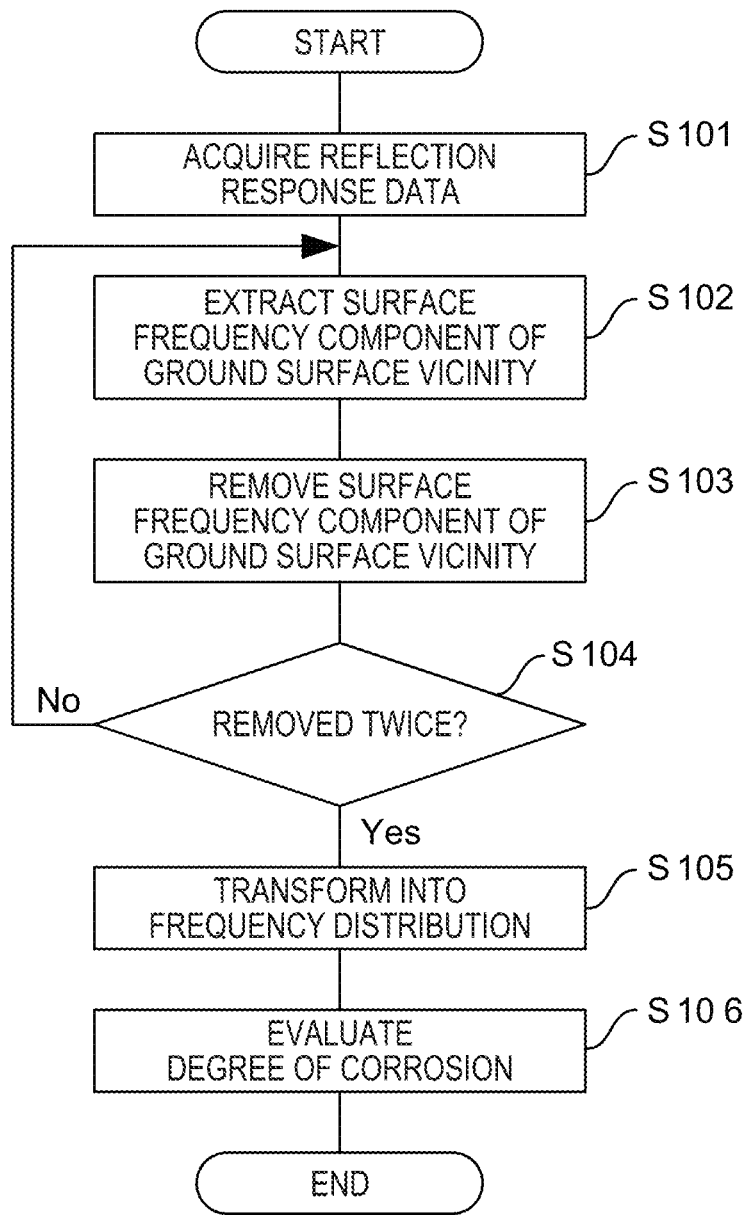
FIG. 14 is a flowchart illustrating a flow of reinforcement bar corrosion evaluation processing by an evaluation device.

FIG. 14 is a flowchart illustrating a flow of reinforcement bar corrosion evaluation processing by the evaluation device 10. The CPU 11 reads the reinforcement bar corrosion evaluation program from the ROM 12 or the storage 14, and performs the reinforcement bar corrosion evaluation processing by expanding and executing the program in the RAM 13.

The CPU 11 acts as the acquisition section 100 and acquires reflection response data relating to the reflection response from the RC deck bridge to the electromagnetic waves from the electromagnetic wave device 20 (step S101).

Next continuing to step S101, the CPU 11 extracts the surface frequency components of the ground surface vicinity from the reflection response data (step S102). Specifically, the CPU 11 transforms the acquired reflection response data into time-frequency characteristics using an S Transform. The CPU 11 extracts the surface frequency components of the ground surface vicinity time positions from the time-frequency characteristics of the reflection response data. The ground surface vicinity time position depends on the characteristics of the electromagnetic wave device 20 such as, for example, a delay in a cable connected to a sensor, or a timing of transmitting the electromagnetic waves from the antenna and receiving the reflection wave, or a distance between the antenna of the electromagnetic wave device 20 and the surface of the RC deck bridge, and may be a position corresponding to a 5 nanosecond vicinity in the time-frequency graph.

Next in continuation from step S102, the CPU 11 removes the surface frequency components of the ground surface vicinity extracted at step S102 from the reflection response data (step S103). Specifically, the CPU 11 transforms the ground surface vicinity surface frequency components extracted at step S102 into a time domain waveform using an inverse FFT, and subtracts the waveform after transformation from the reflection response data.

Next in continuation from step S103, the CPU 11 determines whether or not removal of surface frequency components has been executed twice (step S104). In cases in which determination is that the removal of surface frequency components has not been executed twice (step S104: NO), the CPU 11 executes the processing of step S102 and step S103 once more. In cases in which determination is that the removal of surface frequency components has been executed twice (step S104: YES), the CPU 11 transforms the internal frequency components after removal of the surface frequency components into a frequency distribution (step S105). Specifically, the CPU 11 transforms the internal frequency components after removal of the surface frequency components into a time-frequency distribution, and then further transforms this into a frequency distribution.

Next in continuation from step S105, the CPU 11 evaluates the degree of corrosion of the reinforcement bar based on the frequency distribution of the internal frequency components (step S106). Specifically, the CPU 11 evaluates the degree of corrosion of reinforcement bar in the RC deck panels by applying the evaluation standard described above to the frequency distribution of the internal frequency components to determine the corrosion grade of the reinforcement bar in the RC deck panels.

By the CPU 11 executing the cycle of processing illustrated in FIG. 14, the evaluation device 10 according to the present exemplary embodiment is able to efficiently and quantitatively evaluate the degree of corrosion of reinforcement bar in RC deck panels non-destructively.

Note that although in the cycle of processing illustrated in FIG. 14 the surface frequency components of the ground surface vicinity are transformed into a time domain waveform using an inverse FFT, and the processing of subtraction of the waveform after transformation from the reflection response data is repeated twice, the present invention is not limited to this example. The CPU 11 may perform the extraction and removal of ground surface vicinity surface frequency components in a frequency domain. The CPU 11 may also perform a transformation into a time domain waveform using an inverse FFT after repeating the extraction and removal of the ground surface vicinity surface frequency components twice in a frequency domain.

The CPU 11 may execute the cycle of processing illustrated in FIG. 14 in real-time, or the electromagnetic wave device 20 may save data of reflection waves received from the RC deck bridge in the storage 14, and then execute extraction of data from the storage 14 at a freely selected timing.

Next examples will be given of reinforcement bar corrosion evaluation by the evaluation device 10.

Figure 15:
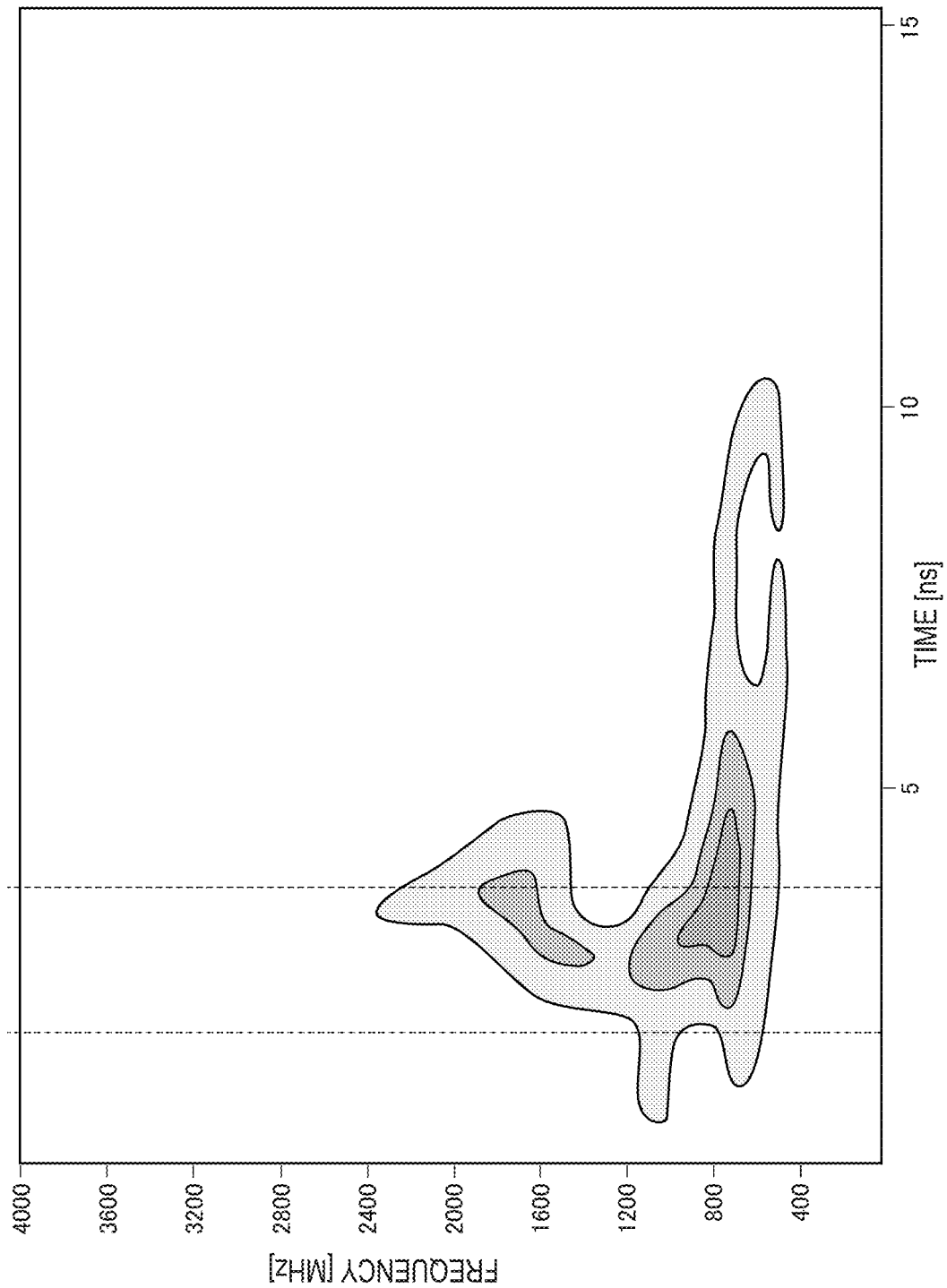
FIG. 15 is an example of a time-frequency distribution graph of internal frequency components of an RC deck panel.
Figure 16:
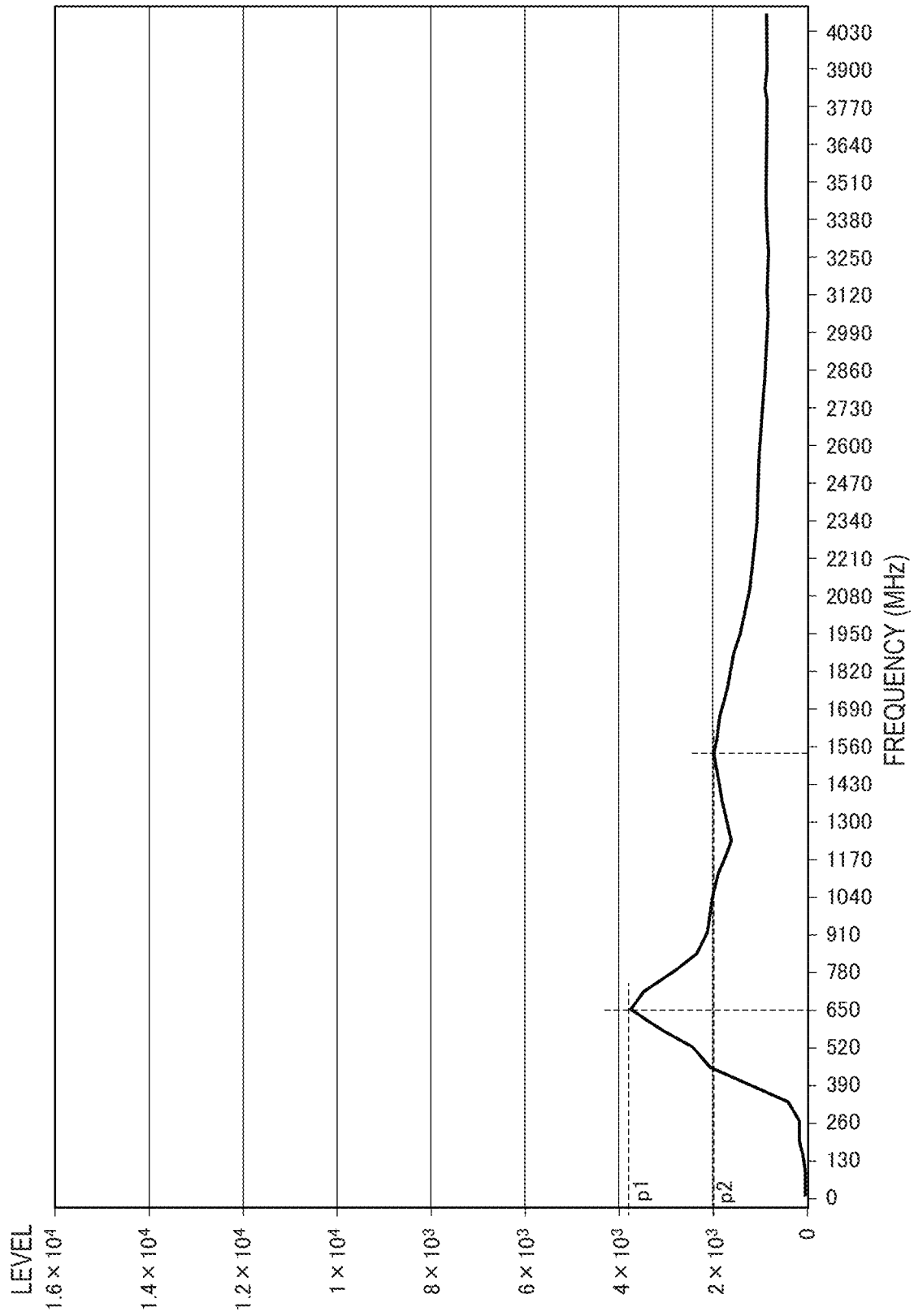
FIG. 16 is a frequency distribution graph of the time-frequency distribution of FIG. 15 transformed into a frequency distribution.
Figure 17:
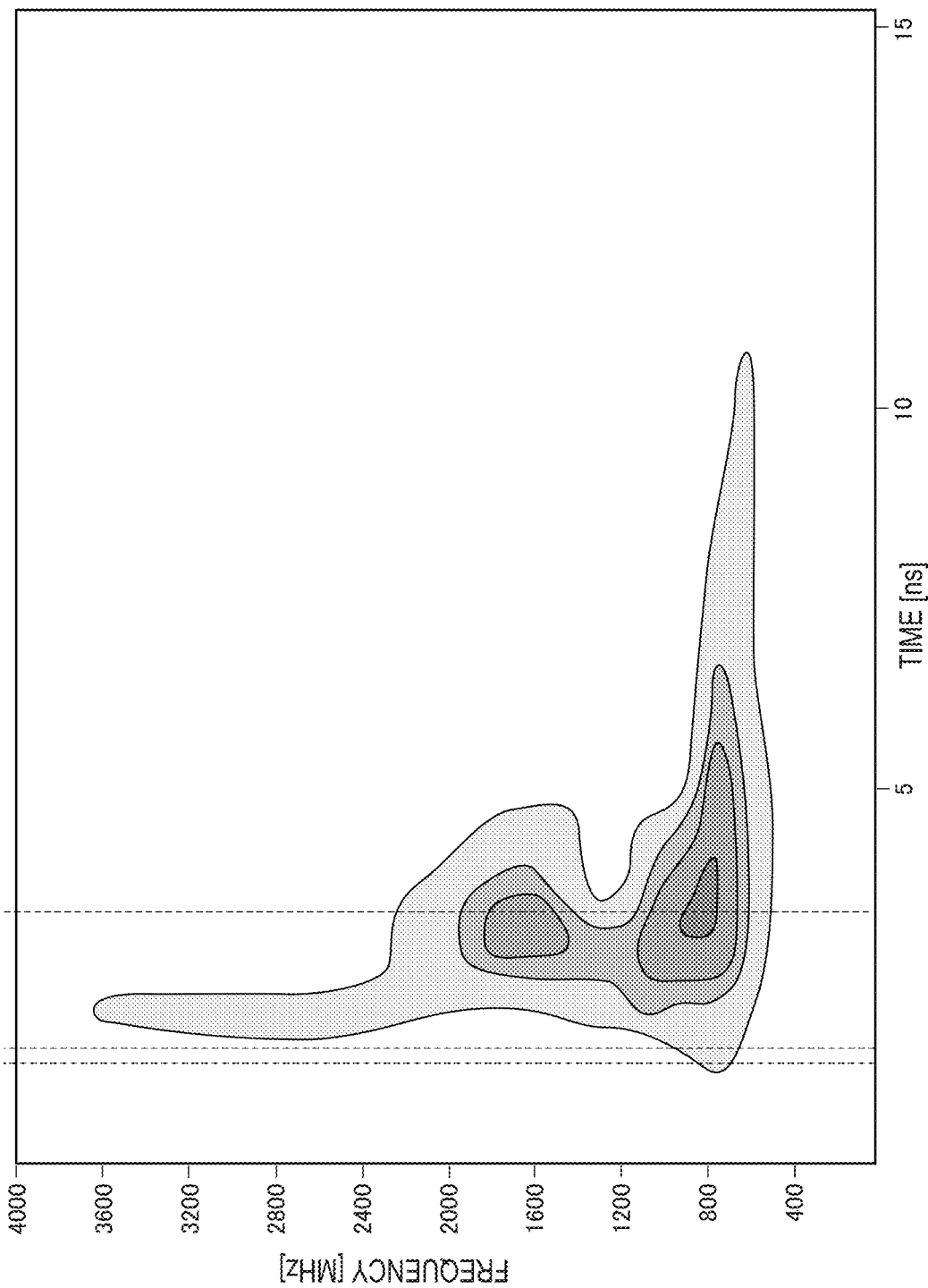
FIG. 17 is an example of a time-frequency distribution graph of internal frequency components of an RC deck panel.
Figure 18:
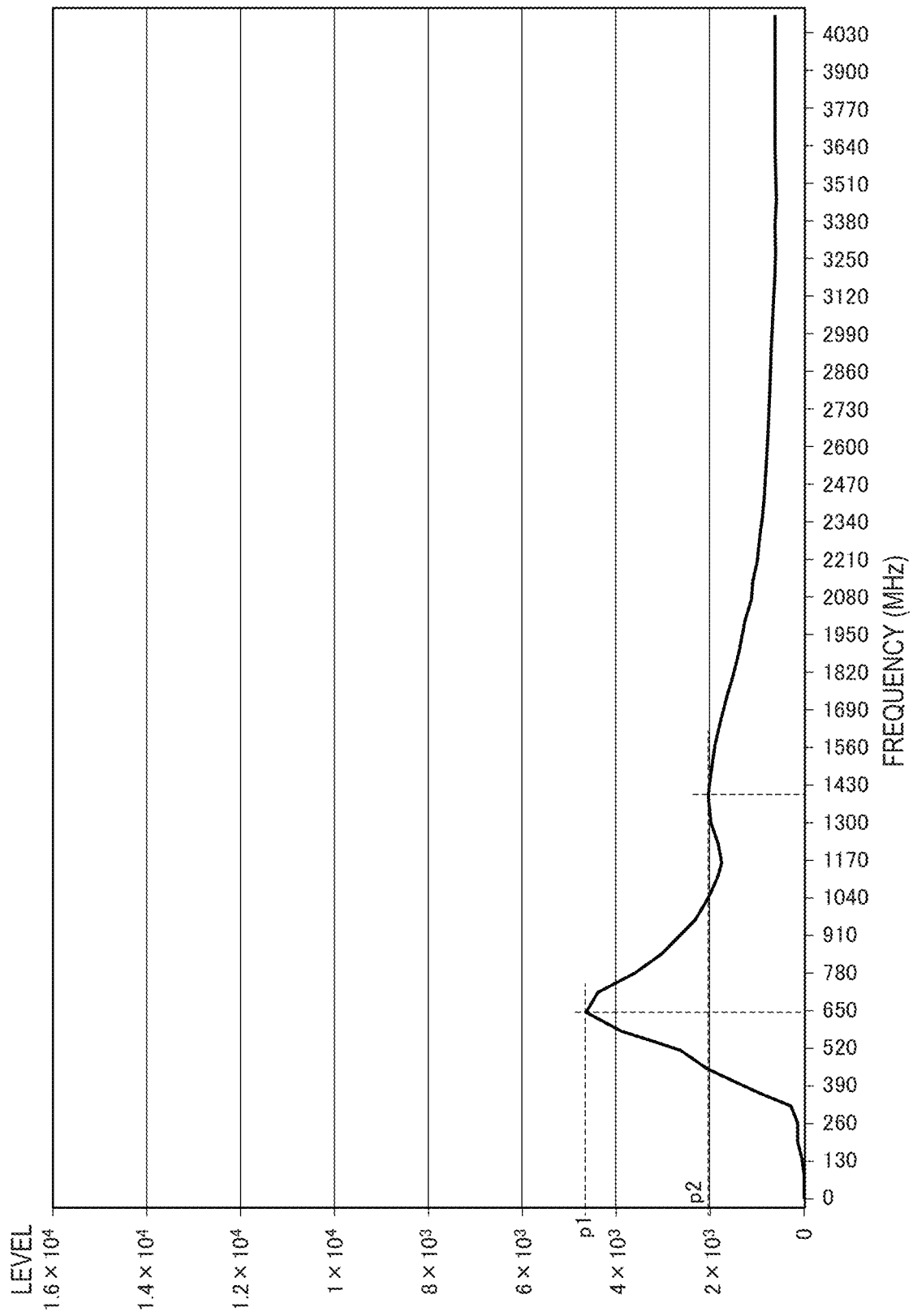
FIG. 18 is a frequency distribution graph of the time-frequency distribution of FIG. 17 transformed into a frequency distribution.
Figure 19:
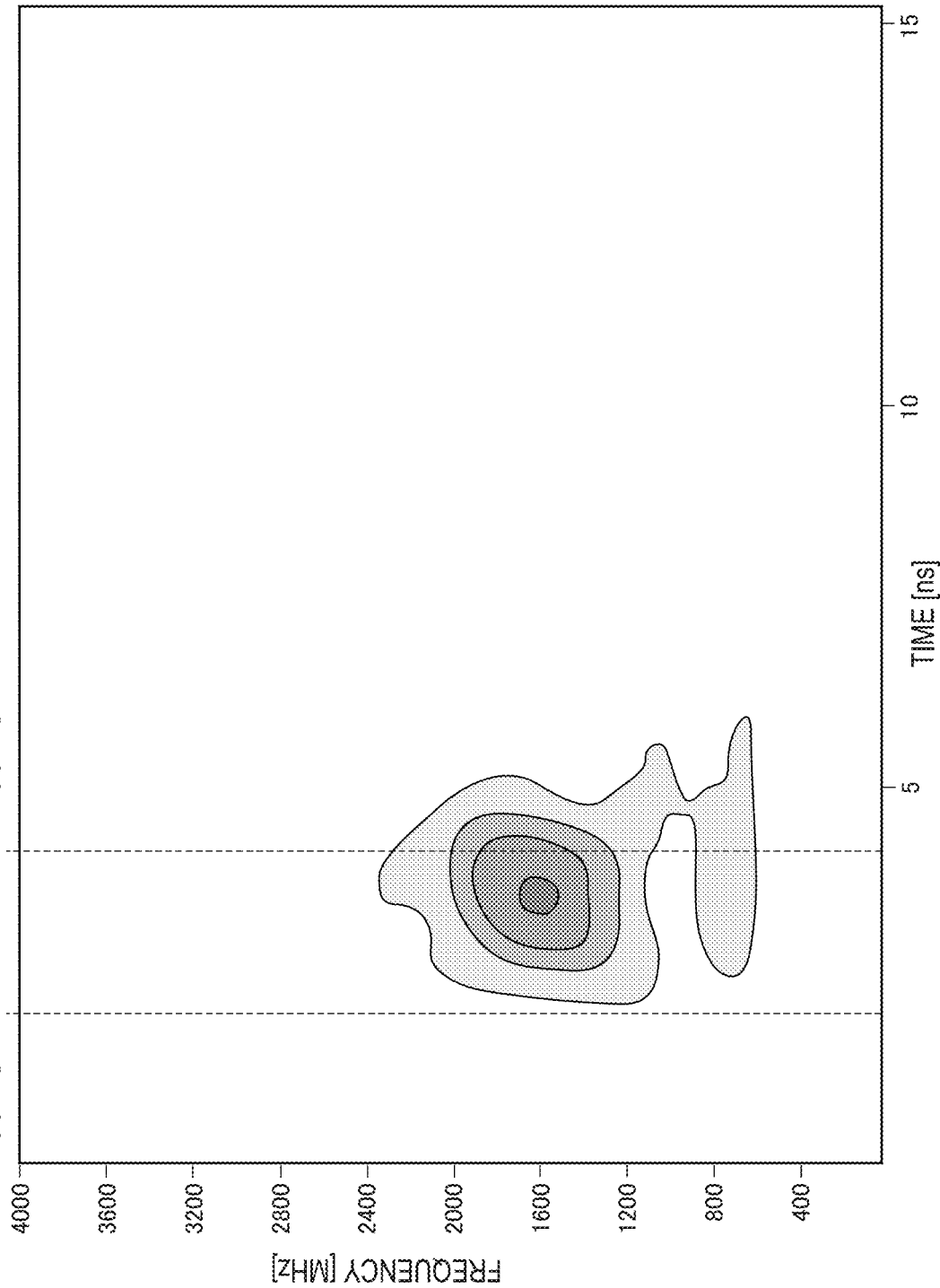
FIG. 19 is an example of a time-frequency distribution graph of internal frequency components of an RC deck panel.
Figure 20:
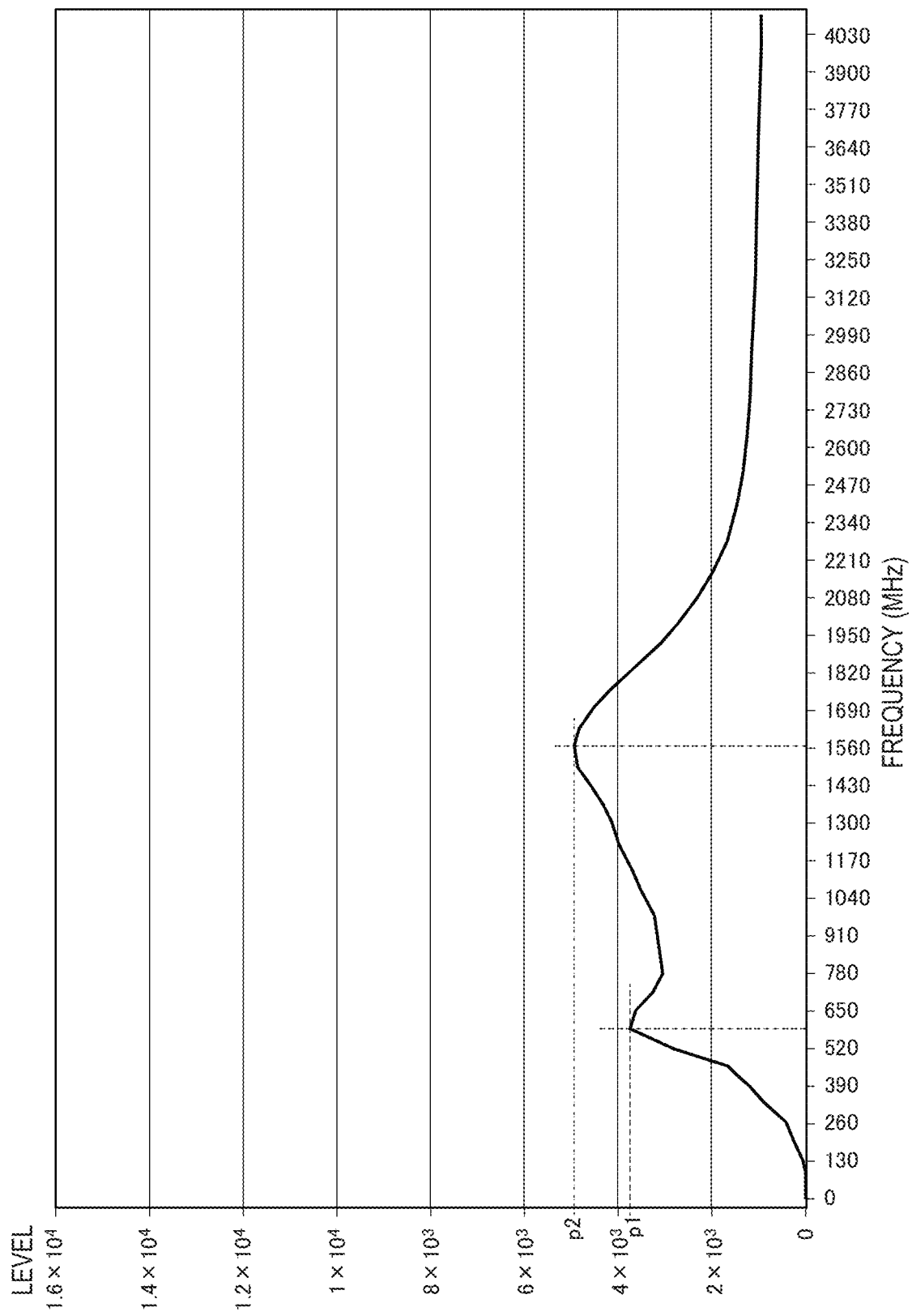
FIG. 20 is a frequency distribution graph of the time-frequency distribution of FIG. 19 transformed into a frequency distribution.

FIG. 15, FIG. 17, and FIG. 19 are examples of the internal frequency components of respective RC deck panels in time-frequency distribution graphs illustrated by contour plots. FIG. 16 is a frequency distribution graph obtained by transforming the time-frequency distribution illustrated in FIG. 15 into a frequency distribution graph. FIG. 18 is a frequency distribution graph obtained by transforming the time-frequency distribution illustrated in FIG. 17 into a frequency distribution graph. FIG. 20 is a frequency distribution graph obtained by transforming the time-frequency distribution illustrated in FIG. 19 into a frequency distribution graph.

In the time-frequency distributions illustrated in FIG. 15 and FIG. 17, the intensity of the first frequency band is strong, and the intensity of the second frequency band is weak. In contrast, in the time-frequency distribution illustrated in FIG. 19, the intensity of the first frequency band is weaker and the intensity of the second frequency band is stronger than in the time-frequency distributions illustrated in FIG. 15 and FIG. 17.

Looking at the time-frequency distribution illustrated in FIG. 15 reveals a peak in intensity at the vicinity of 800 MHz in the vicinity of the reinforcement bar depth. It is moreover apparent that the waveform of the distribution is distorted compared to that of the healthy RC deck panel. At shallower positions from the reinforcement bar vicinity, a distribution in the vicinity of from 1200 MHz to 2000 MHz is brought out into relief compared to the healthy RC deck panel. It is thought this is because reflection is weak at the reinforcement bar, and the frequency distribution shape is distorted due to the influence of peripheral concrete, increasing the distribution at locations shallower than the reinforcement bar.

The first measurement peak value p1 in the frequency distribution illustrated in FIG. 16 is half, or less than half of the first measurement peak value p1 in the frequency distribution illustrated in FIG. 13. The second measurement peak value p2 in the frequency distribution illustrated in FIG. 16 is less than the first measurement peak value p1. Thus from the frequency distribution illustrated in FIG. 16 the CPU 11 determines the corrosion grade of the reinforcement bar being evaluated to be grade 2 or grade 3.

From looking at the time-frequency distribution illustrated in FIG. 17 it is apparent that, similarly to FIG. 15, there is a peak at an intensity in the vicinity of 800 MHz of the reinforcement bar depth vicinity. Moreover, the waveform of the distribution appears distorted compared to the healthy RC deck panel. At shallower positions from the reinforcement bar depth, a distribution in the vicinity of from 1200 MHz to 2000 MHz is brought out into relief compared to the healthy RC deck panel, and it is brought out more clearly into relief than in FIG. 15. It is thought this is because reflection at the reinforcement bar becomes weaker as the corrosion of the reinforcement bar progresses, and so the frequency distribution waveform is distorted due to influence from the peripheral concrete, with a further increase in the distribution for the locations shallower than the reinforcement bar.

The first measurement peak value p1 in the frequency distribution illustrated in FIG. 18 is half, or less than half, the first measurement peak value p1 in the frequency distribution illustrated in FIG. 13. The second measurement peak value p2 in the frequency distribution illustrated in FIG. 18 is less than the first measurement peak value p1. Thus from the frequency distribution illustrated in FIG. 18 the CPU 11 determines the corrosion grade of the reinforcement bar being evaluated to be grade 2 or grade 3.

Looking at the time-frequency distribution illustrated in FIG. 19, there is no peak in the distribution at the vicinity of 800 MHz of the reinforcement bar depth vicinity, and in contrast to when healthy, a large peak appears in the distribution at the vicinity of 1200 MHz to 2000 MHz at positions shallower than the reinforcement bar depth. It is thought this is because the reflection of the reinforcement bar becomes weaker as the corrosion of the reinforcement bar progresses, and reflections are captured by cracks and damage in the concrete at positions shallower than the reinforcement bar depth.

The first measurement peak value p1 in the frequency distribution illustrated in FIG. 20 is half, or less than half of the first measurement peak value p1 in the frequency distribution illustrated in FIG. 13. The second measurement peak value p2 in the frequency distribution illustrated in FIG. 20 is greater than the first measurement peak value p1. Thus from the frequency distribution illustrated in FIG. 20 the CPU 11 determines the corrosion grade of the reinforcement bar being evaluated to be grade 4.

In reality, FIG. 15 and FIG. 16 are distribution graphs for when electromagnetic waves are irradiated into a RC deck bridge in which the corrosion grade of the reinforcement bar is grade 2, and FIG. 17 and FIG. 18 are distribution graphs for when electromagnetic waves are irradiated into a RC deck bridge in which the corrosion grade of the reinforcement bar is grade 3. FIG. 19 and FIG. 20 are distribution graphs for when electromagnetic waves are irradiated into a RC deck bridge in which the corrosion grade of the reinforcement bar is grade 4. Thus the evaluation device 10 according to the present exemplary embodiment is able to evaluate the degree of corrosion of reinforcement bar from the frequency distribution obtained when electromagnetic waves are irradiated into a RC deck bridge.

Explanation continues with a case in which the removal of surface frequency components is performed only once, as a comparative example to when performed twice.

Figure 22:
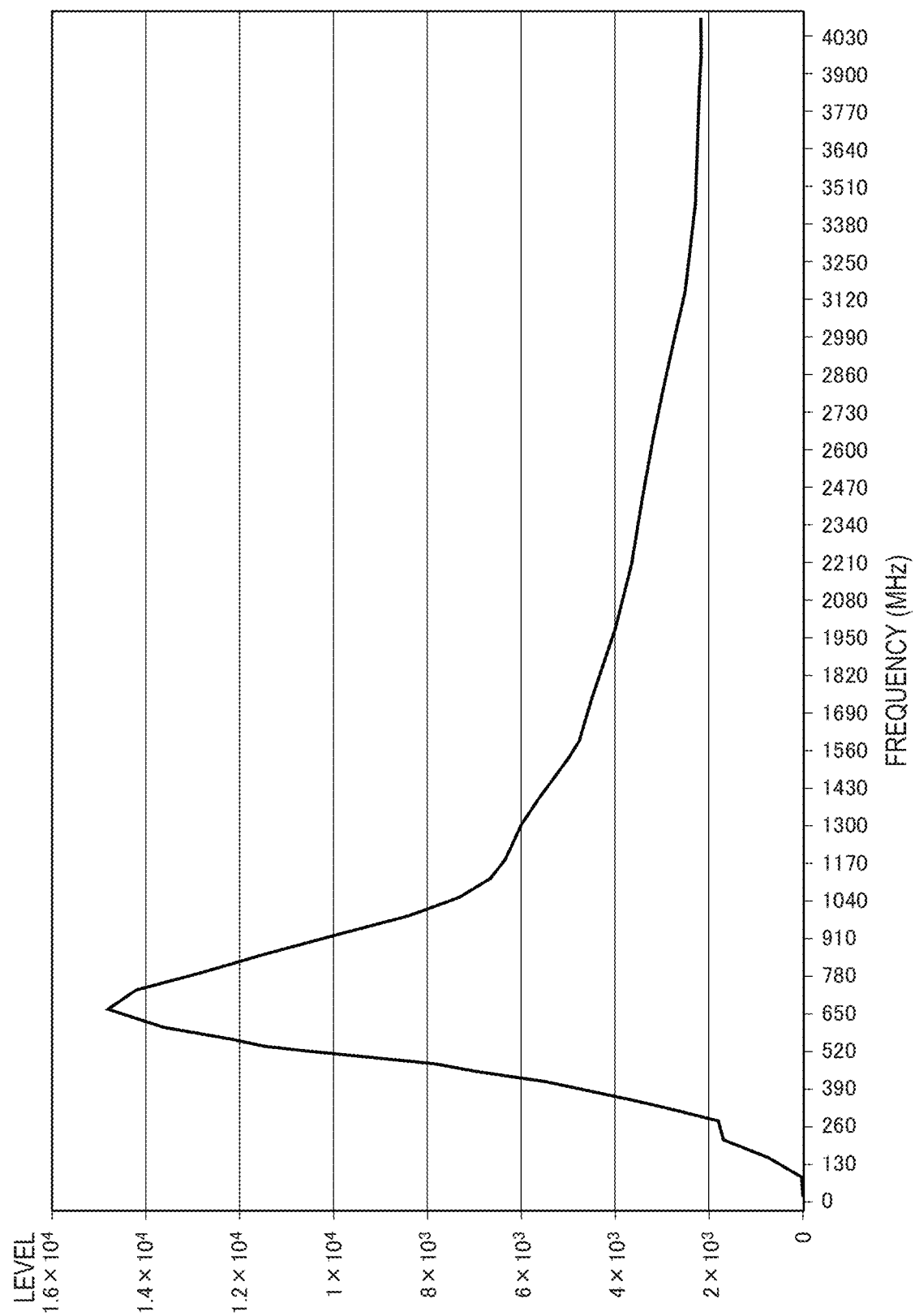
FIG. 22 is a frequency distribution graph of the time-frequency distribution of FIG. 21 transformed into a frequency distribution.
Figure 23:
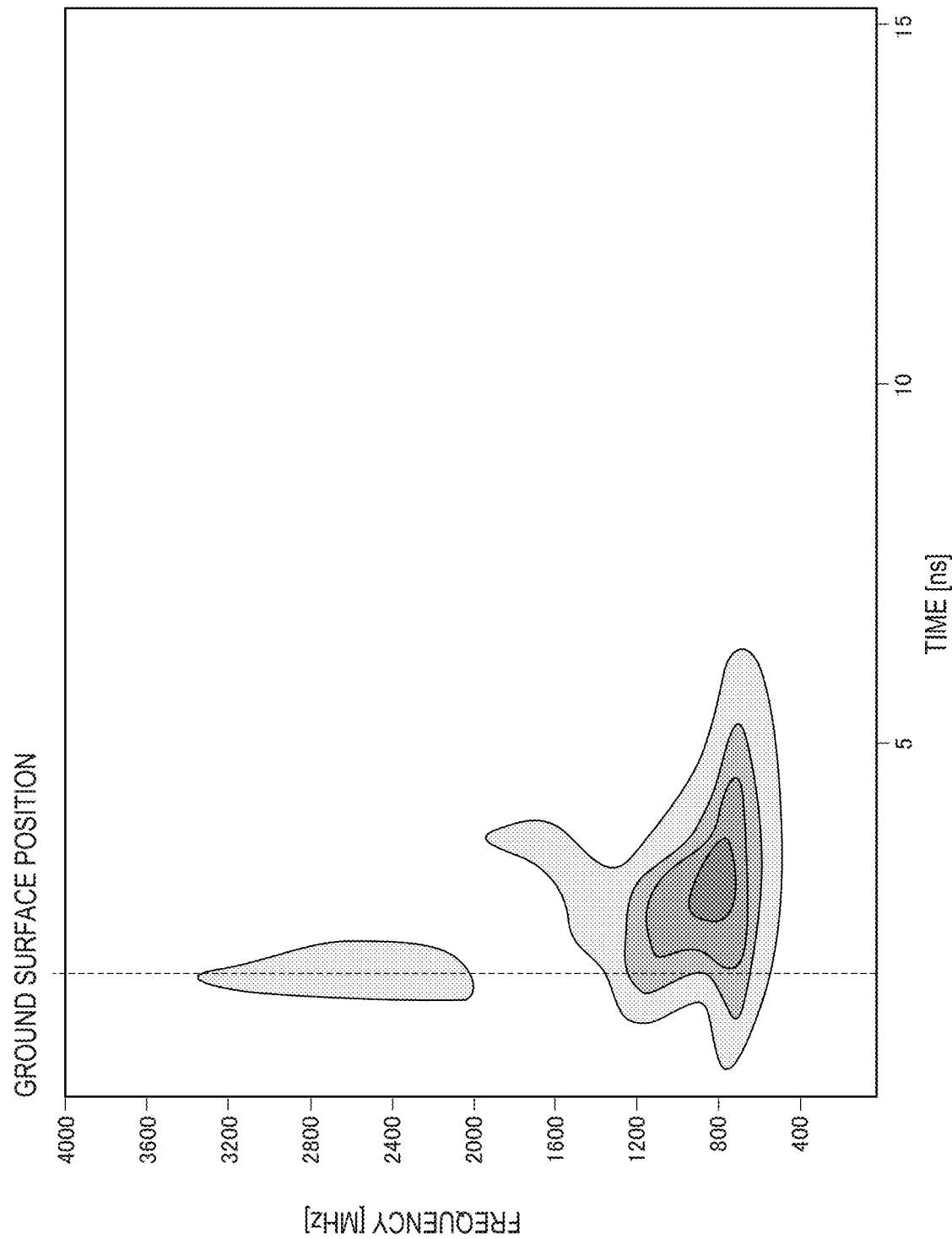
FIG. 23 is an example of a time-frequency distribution graph of internal frequency components of an RC deck panel.
Figure 24:
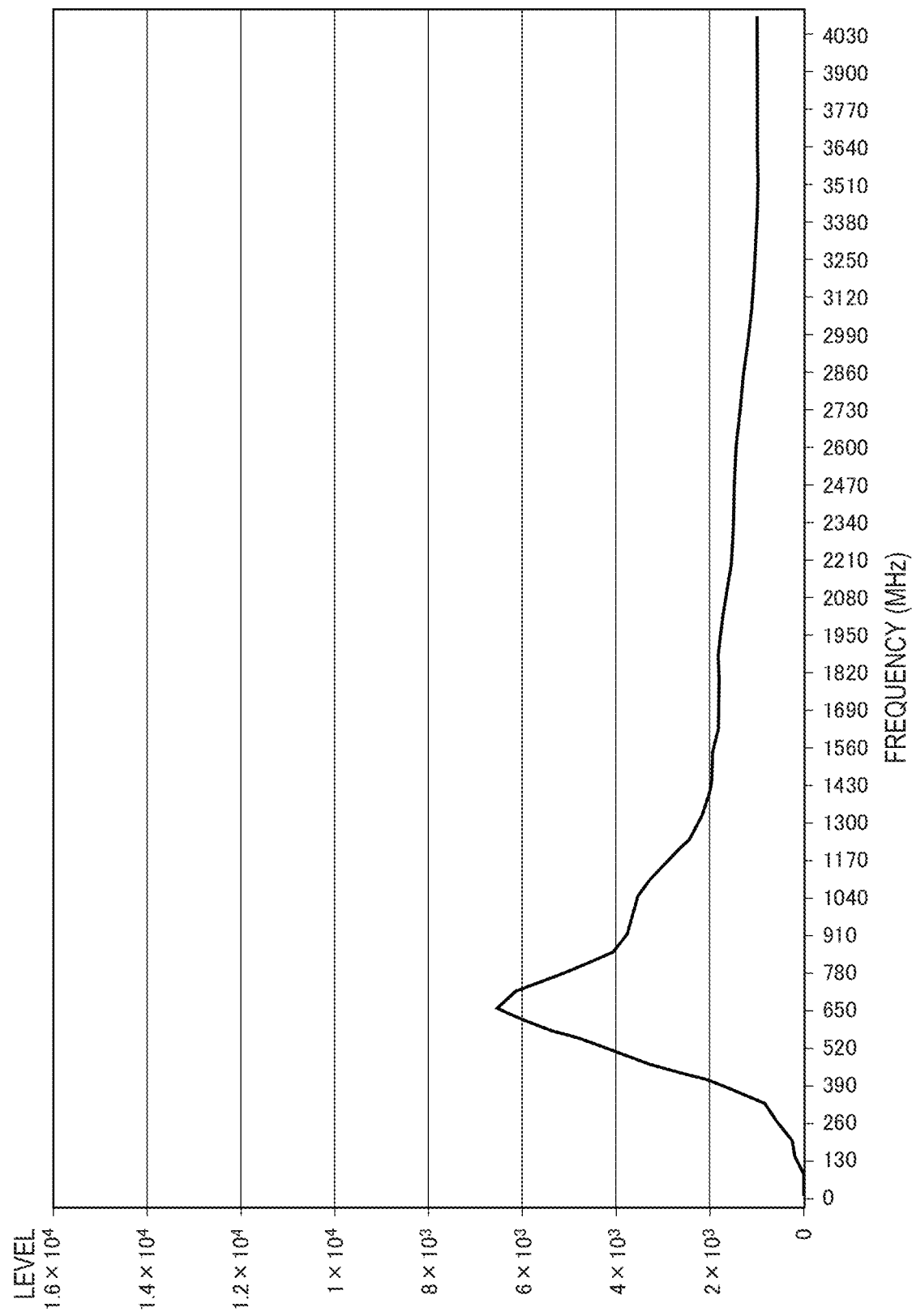
FIG. 24 is a frequency distribution graph of the time-frequency distribution of FIG. 23 transformed into a frequency distribution.
Figure 25:
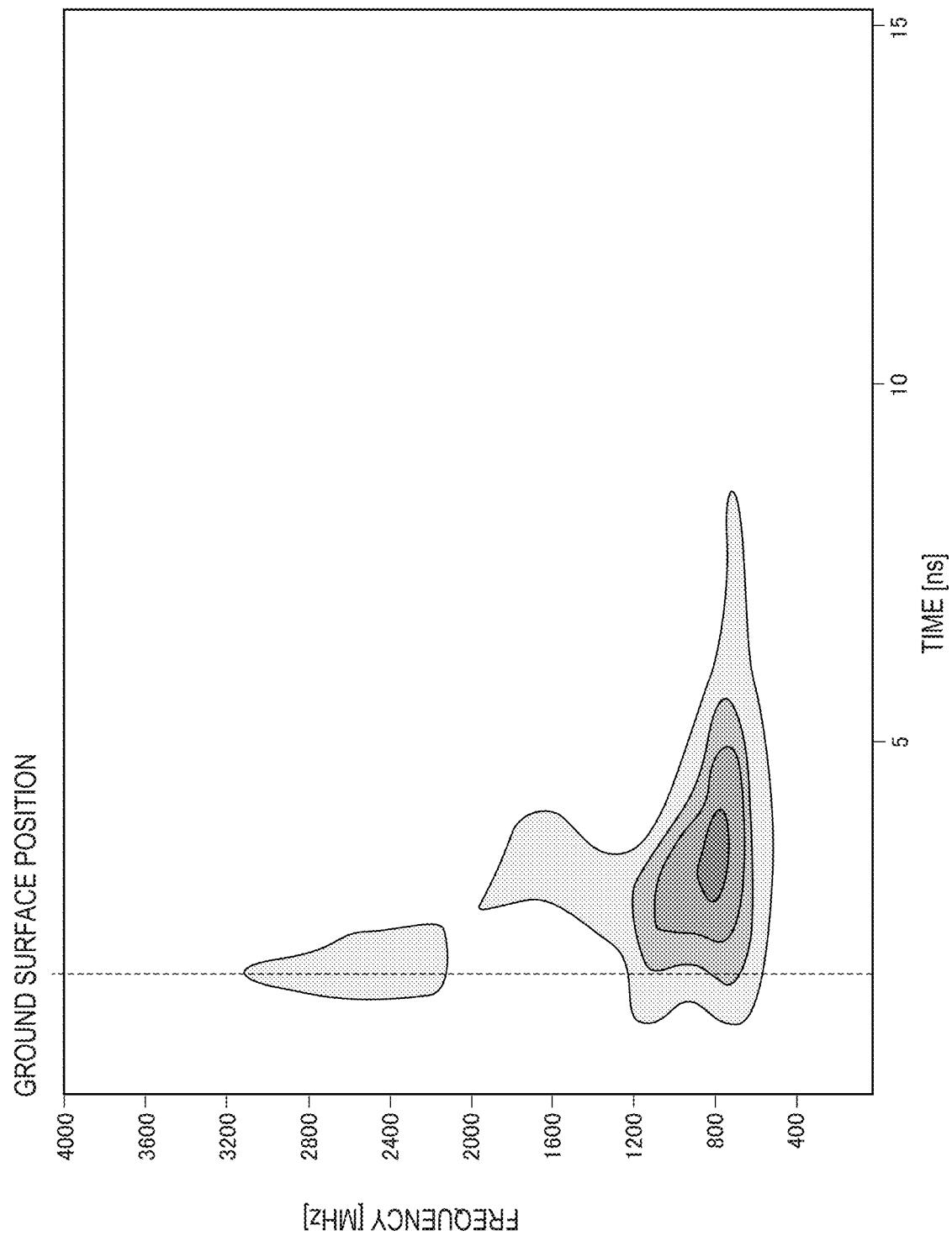
FIG. 25 is an example of a time-frequency distribution graph of internal frequency components of an RC deck panel.
Figure 26:
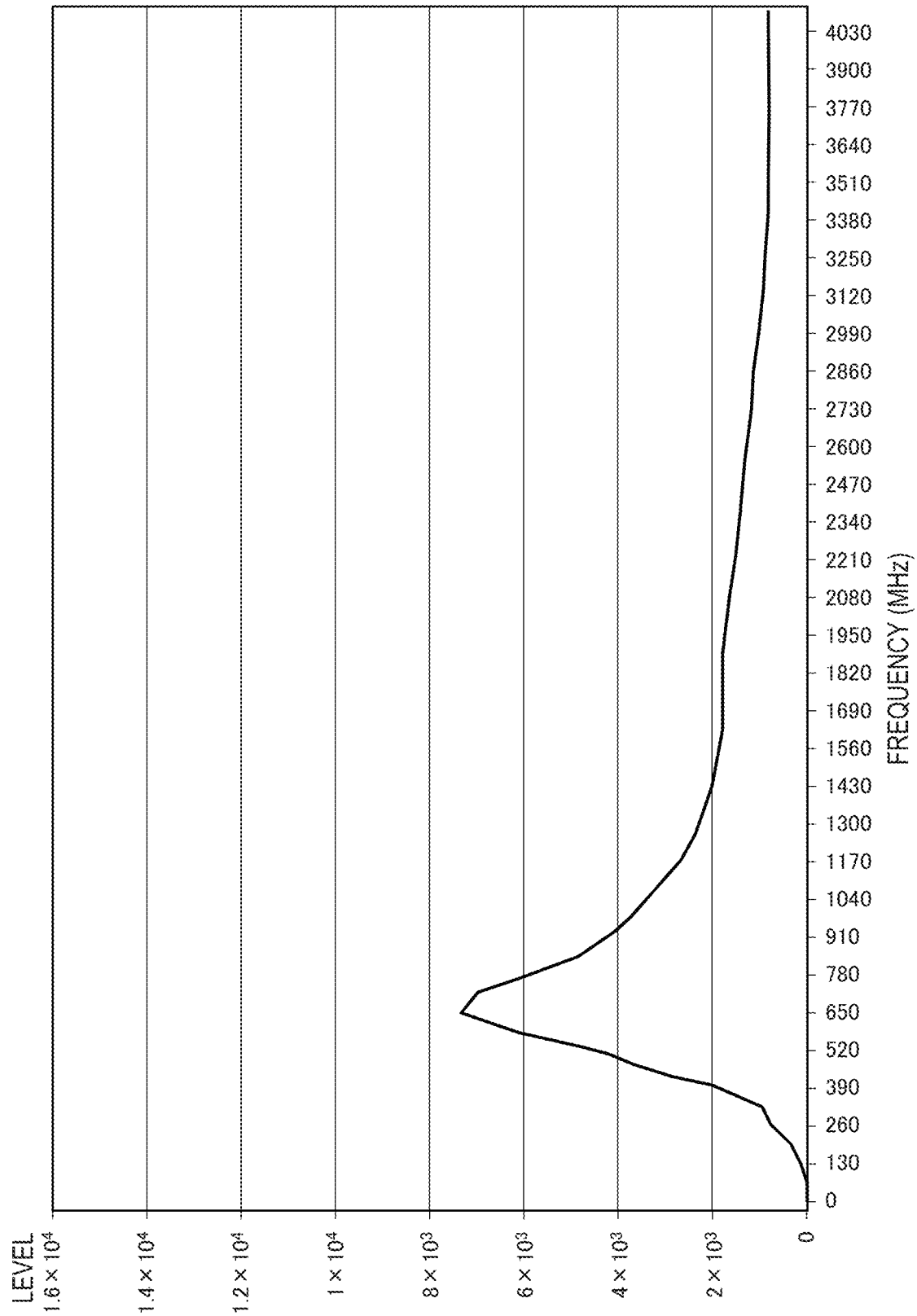
FIG. 26 is a frequency distribution graph of the time-frequency distribution of FIG. 25 transformed into a frequency distribution.

FIG. 21, FIG. 23, FIG. 25, and FIG. 27 are respectively the examples of a time-frequency distribution graph expressed as a contour plot of the internal frequency components of the RC deck panel, in case in which the removal of surface frequency components of RC deck bridge is performed only once. FIG. 22 is a frequency distribution graph obtained by transforming the time-frequency distribution illustrated in FIG. 21 into a frequency distribution. FIG. 24 is a frequency distribution graph obtained by transforming the time-frequency distribution illustrated in FIG. 23 into a frequency distribution. FIG. 26 is a frequency distribution graph obtained by transforming the time-frequency distribution illustrated in FIG. 25 into a frequency distribution. FIG. 28 is a frequency distribution graph obtained by transforming the time-frequency distribution illustrated in FIG. 27 into a frequency distribution.

Figure 21:
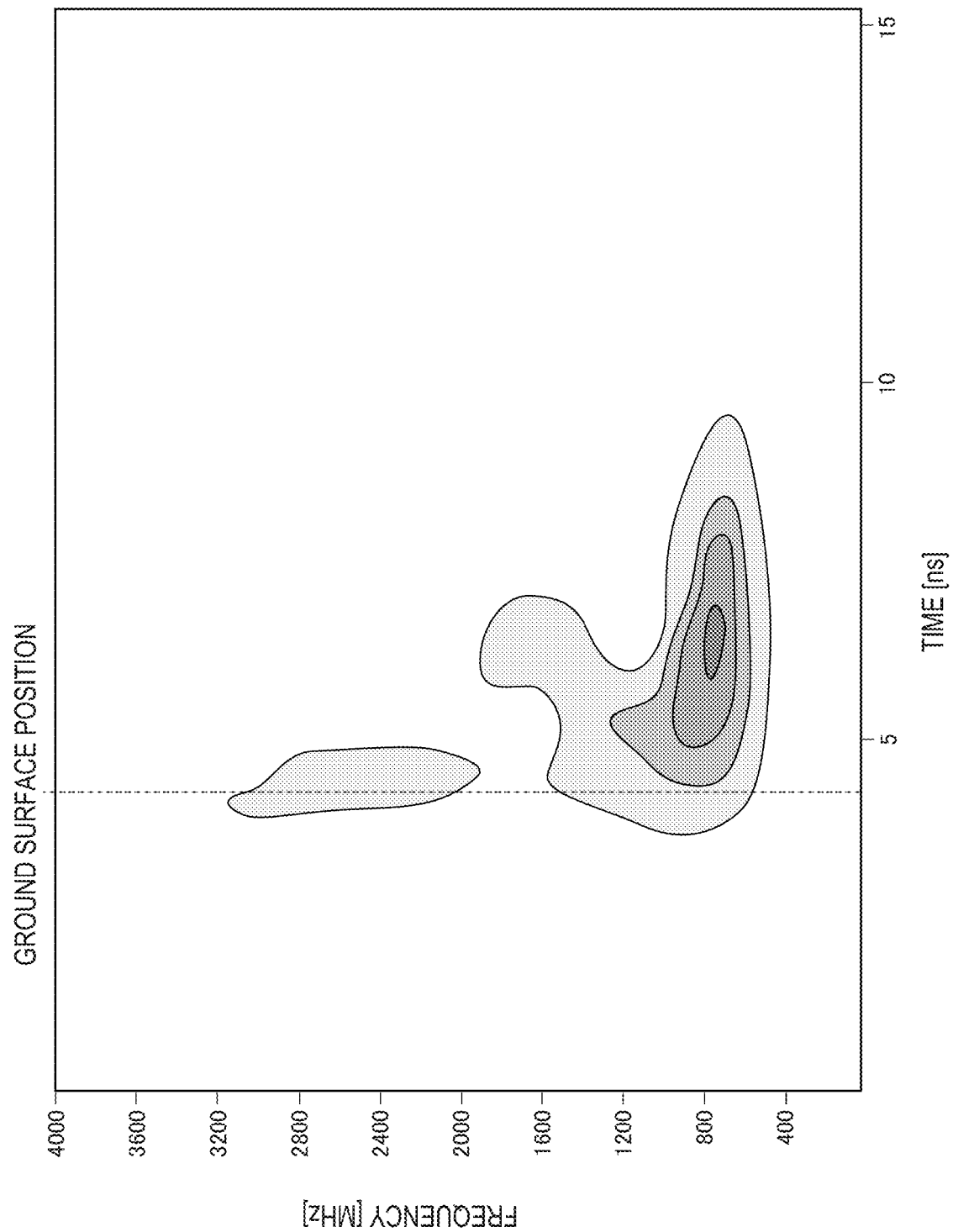
FIG. 21 is an example of a time-frequency distribution graph of internal frequency components of an RC deck panel.
Figure 27:
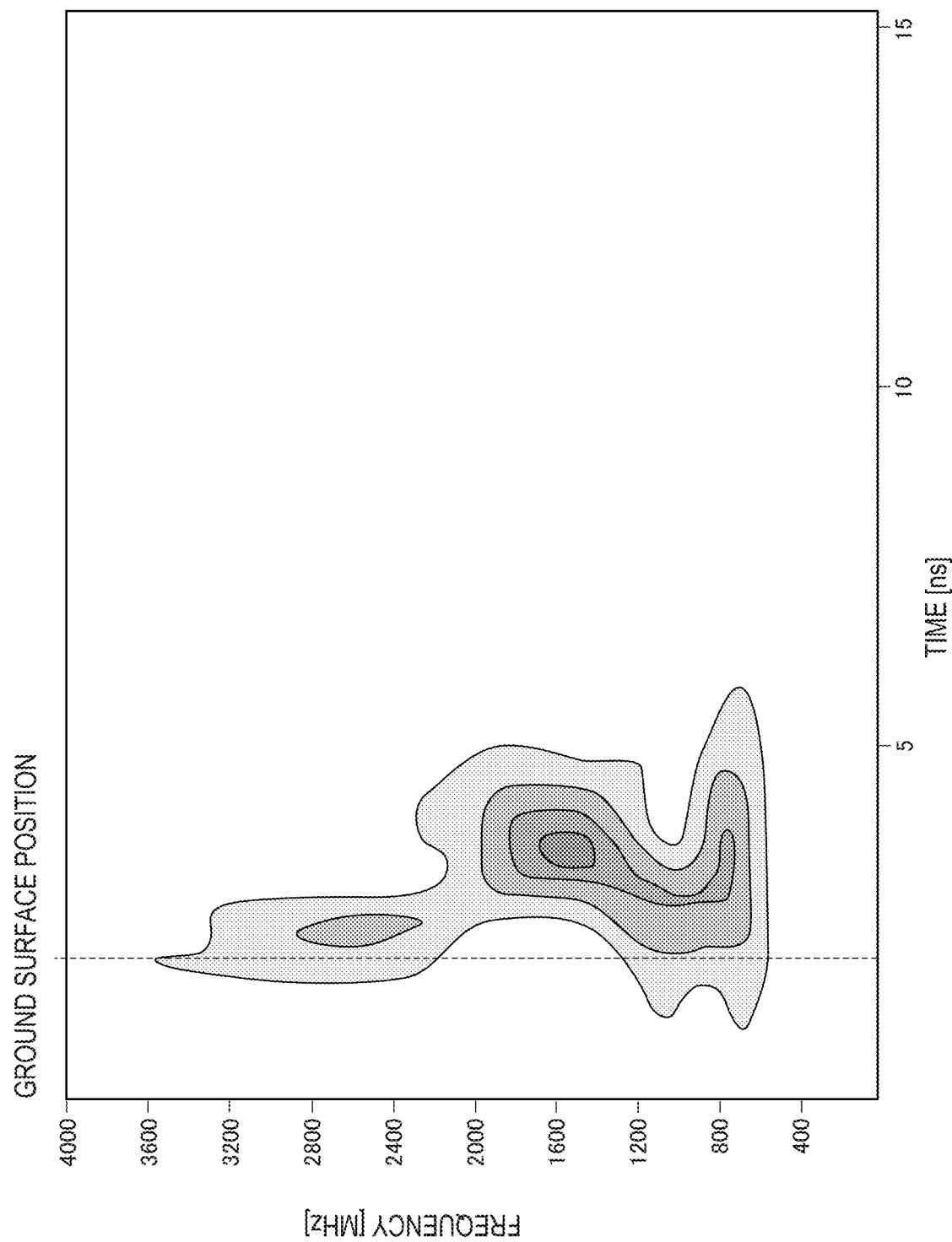
FIG. 27 is an example of a time-frequency distribution graph of internal frequency components of an RC deck panel.

FIG. 21 and FIG. 22 are, similarly to the distribution graphs of FIG. 12 and FIG. 13, distribution graphs obtained from reflection response data from a healthy RC deck panel. FIG. 23 and FIG. 24 are, similarly to the distribution graphs of FIG. 15 and FIG. 16, distribution graphs obtained from reflection response data from an RC deck panel having a corrosion grade of grade 2. FIG. 25 and FIG. 26 are, similarly to the distribution graphs of FIG. 17 and FIG. 18, distribution graphs obtained from reflection response data from an RC deck panel having a corrosion grade of grade 3. FIG. 27 and FIG. 28 are, similarly to the distribution graphs of FIG. 19 and FIG. 20, distribution graphs obtained from reflection response data from an RC deck panel having a corrosion grade of grade 4.

Looking at the frequency distribution graph illustrated in FIG. 22 reveals a clear peak value observable at a first frequency band, however there is no clear peak value observable in the second frequency band. Similarly, looking at the frequency distribution graphs illustrated in FIG. 24 and FIG. 26 reveals a clear peak value observable at a first frequency band, however there is no clear peak value observable in the second frequency band. Looking at the frequency distribution graph illustrated in FIG. 28 reveals clear peak values observable at both a first frequency band and a second frequency band, however a reversal is not seen in the magnitude relationship between the first measurement peak value in the first frequency band and the second measurement peak value in the second frequency band.

These phenomena are thought to be caused by not completely removing the surface frequency components by performing removal processing only once. Thus in the evaluation device 10 according to the present exemplary embodiment the removal of surface frequency components is performed twice to enable evaluation of the degree of corrosion of reinforcement bar to be executed with high accuracy based on the frequency distributions of the internal frequency components.

Note that the reinforcement bar corrosion evaluation processing executed by the CPU reading and executing software (a program) in each of the exemplary embodiments described above may also be executed by various processors other than a CPU. Examples of such include programmable logic devices (PLD) that allow circuit configuration to be modified post-manufacture, such as a field-programmable gate array (FPGA), and dedicated electronic circuits, these being processors including a circuit configuration custom-designed to execute specific processing, such as an application specific integrated circuit (ASIC). Moreover, the reinforcement bar corrosion evaluation processing may be executed by any one of these various types of processors, or may be executed by a combination of two or more of the same type or different types of processors (such as plural FPGAs, or a combination of a CPU and an FPGA). The hardware structure of these various types of processors is more specifically an electric circuit combining circuit elements such as semiconductor elements.

Moreover, although explanation in each of the exemplary embodiments is of a mode in which the reinforcement bar corrosion evaluation program for executing the reinforcement bar corrosion evaluation processing is pre-stored (installed) on the ROM or storage, there is no limitation thereto. The program may be distributed in a format recorded on a recording medium such as a compact disc read only memory (CD-ROM), a digital versatile disc read only memory (DVD-ROM), or universal serial bus (USB) memory. The program may also be in a format downloadable from an external device over a network.

The invention claimed is:

1. A reinforcement bar corrosion evaluation device for evaluating a degree of corrosion of reinforcement bar in a reinforced concrete deck bridge, the reinforcement bar corrosion evaluation device comprising:

an acquisition section configured to acquire reflection response data related to a reflection response of electromagnetic waves irradiated from a surface of the reinforced concrete deck bridge in a depth direction of the reinforced concrete deck bridge;

a removal section configured to remove a surface frequency component obtained by the electromagnetic waves being reflected at the surface of the reinforced concrete deck bridge from a frequency distribution of a reflection response expressing the reflection response data acquired by the acquisition section; and an evaluation section configured to evaluate a degree of corrosion of the reinforcement bar in the reinforced concrete deck bridge by using a first measurement peak value in the frequency distribution of the reflection response from which the surface frequency component has been removed by the removal section, which is a peak value of a level of a frequency component of a first frequency band, and using a second measurement peak value therein, which is a peak value of a level of a frequency component of a second frequency band that is a higher frequency band than the first frequency band.

2. The reinforcement bar corrosion evaluation device of claim 1, wherein the removal section further removes a frequency component obtained for the electromagnetic waves reflected at the surface of the reinforced concrete deck bridge from the frequency distribution of the reflection response from which the surface frequency component has been removed.

3. The reinforcement bar corrosion evaluation device of claim 1, wherein the evaluation section compares the first measurement peak value and the second measurement peak value and evaluates the degree of corrosion of the reinforcement bar in the reinforced concrete deck bridge based on a magnitude relationship between the first measurement peak value and the second measurement peak value.

4. The reinforcement bar corrosion evaluation device of claim 3, wherein the evaluation section evaluates the degree of corrosion to be that corrosion of the reinforcement bar has progressed in the reinforced concrete deck bridge in a case in which the second measurement peak value is greater than the first measurement peak value.

5. The reinforcement bar corrosion evaluation device of claim 1, wherein the evaluation section uses, as a standard value, a peak value of a level of the first frequency band in a standard frequency distribution, which is a frequency distribution of a reflection response obtained by removing the frequency component from the reflection response obtained by irradiating electromagnetic waves against an un-deteriorated reinforced concrete deck bridge, and evaluates the degree of corrosion of the reinforcement bar in the reinforced concrete deck bridge by comparing the first measurement peak value against the standard value.

6. The reinforcement bar corrosion evaluation device of claim 5, wherein the evaluation section uses a prescribed proportion with respect to the standard value as a threshold, and evaluates the degree of corrosion as corrosion having progressed in the reinforcement bar in the reinforced concrete deck bridge in a case in which the first measurement peak value is less than the threshold.

7. The reinforcement bar corrosion evaluation device of claim 1, wherein the evaluation section evaluates the degree of corrosion of the reinforcement bar in the reinforced concrete deck bridge at a plurality of positions on the surface of the reinforced concrete deck bridge.

8. A reinforcement bar corrosion evaluation method for evaluating a degree of corrosion of reinforcement bar in a reinforced concrete deck bridge, the reinforcement bar corrosion evaluation method comprising:

an acquisition step of acquiring reflection response data related to a reflection response of electromagnetic waves irradiated from a surface of the reinforced concrete deck bridge in a depth direction of the reinforced concrete deck bridge;

a removal step of removing a surface frequency component obtained by the electromagnetic waves being reflected at the surface of the reinforced concrete deck bridge from a frequency distribution of a reflection response expressing the reflection response data acquired by the acquisition step; and an evaluation step of evaluating a degree of corrosion of the reinforcement bar in the reinforced concrete deck bridge by using a first measurement peak value in the frequency distribution of the reflection response from which the surface frequency component has been removed by the removal step, which is a peak value of a level of a frequency component of a first frequency band, and using a second measurement peak value therein, which is a peak value of a level of a frequency component of a second frequency band that is a higher frequency band than the first frequency band.

9. A non-transitory computer-readable medium for evaluating a degree of corrosion of reinforcement bar in a reinforced concrete deck bridge, the computer-readable medium storing instructions that, when executed by one or more processors, cause the one or more processors to execute processing comprising:

an acquisition step of acquiring reflection response data related to a reflection response of electromagnetic waves irradiated from a surface of the reinforced concrete deck bridge in a depth direction of the reinforced concrete deck bridge;

a removal step of removing a surface frequency component obtained by the electromagnetic waves being reflected at the surface of the reinforced concrete deck bridge from a frequency distribution of a reflection response expressing the reflection response data acquired by the acquisition step; and an evaluation step of evaluating a degree of corrosion of the reinforcement bar in the reinforced concrete deck bridge by using a first measurement peak value in the frequency distribution of the reflection response from which the surface frequency component has been removed by the removal step, which is a peak value of a level of a frequency component of a first frequency band and using a second measurement peak value therein, which is a peak value of a level of a frequency component of a second frequency band that is a higher frequency band than the first frequency band.

* * * * *